United States Patent
Brenneman et al.

(10) Patent No.: US 10,448,953 B2
(45) Date of Patent: Oct. 22, 2019

(54) METHODS, SYSTEMS AND DEVICES FOR TREATING CARDIAC ARRHYTHMIAS

(71) Applicant: Rox Medical, Inc., San Clemente, CA (US)

(72) Inventors: Rodney Brenneman, San Juan Capistrano, CA (US); Peter Balmforth, Oslo (NO); J. Christopher Flaherty, Auburndale, FL (US)

(73) Assignee: Rox Medical, Inc., San Clemente, CA (US)

( * ) Notice: Subject to any disclaimer, the term of this patent is extended or adjusted under 35 U.S.C. 154(b) by 0 days.

(21) Appl. No.: 14/766,125

(22) PCT Filed: Jan. 16, 2014

(86) PCT No.: PCT/US2014/011912
§ 371 (c)(1),
(2) Date: Aug. 5, 2015

(87) PCT Pub. No.: WO2014/116502
PCT Pub. Date: Jul. 31, 2014

(65) Prior Publication Data
US 2016/0058452 A1    Mar. 3, 2016

Related U.S. Application Data

(60) Provisional application No. 61/755,789, filed on Jan. 23, 2013.

(51) Int. Cl.
A61B 17/11    (2006.01)
A61B 17/00    (2006.01)
(Continued)

(52) U.S. Cl.
CPC ............ *A61B 17/11* (2013.01); *A61B 5/0071* (2013.01); *A61B 5/021* (2013.01); *A61B 5/6876* (2013.01);
(Continued)

(58) Field of Classification Search
CPC ............... A61B 17/11; A61B 5/6876; A61B 2017/00022; A61B 2017/1107; A61B 2017/1139
See application file for complete search history.

(56) References Cited

U.S. PATENT DOCUMENTS 5,445,600 A * 8/1995 Abdulla ............. A61B 17/0057
604/9
5,682,906 A    11/1997 Sterman et al.
(Continued)

FOREIGN PATENT DOCUMENTS

WO    WO-2007005386 A1    1/2007
WO    WO-2011059829 A1    5/2011
WO    WO 2014/052919 A1   4/2014

OTHER PUBLICATIONS

International preliminary report on patentability dated Aug. 6, 2015 for PCT/US2013/011912.
(Continued)

*Primary Examiner* — Anh T Dang
(74) *Attorney, Agent, or Firm* — Wilson Sonsini Goodrich & Rosati

(57) ABSTRACT

Provided is a method of treating cardiac arrhythmia in a patient. The method comprises selecting a patient suffering from a cardiac arrhythmia and creating a flow pathway between a first vascular location and a second vascular location. The first vascular location comprises a source of arterial blood and the second vascular location comprises a
(Continued)

source of venous blood. Systems and devices for creating a flow pathway are also provided.

17 Claims, 9 Drawing Sheets

(51) Int. Cl.
*A61B 17/34* (2006.01)
*A61B 90/00* (2016.01)
*A61B 5/021* (2006.01)
*A61B 5/00* (2006.01)

(52) U.S. Cl.
CPC . *A61B 17/3478* (2013.01); *A61B 2017/00022* (2013.01); *A61B 2017/00526* (2013.01); *A61B 2017/1107* (2013.01); *A61B 2017/1139* (2013.01); *A61B 2090/374* (2016.02); *A61B 2090/376* (2016.02); *A61B 2090/378* (2016.02)

(56) References Cited

U.S. PATENT DOCUMENTS

| | | | |
|---|---|---|---|
| 6,926,690 B2 * | 8/2005 | Renati | A61F 2/2493 604/284 |
| 7,828,814 B2 | 11/2010 | Brenneman et al. | |
| 8,016,782 B2 | 9/2011 | Brenneman et al. | |
| 8,382,697 B2 | 2/2013 | Brenneman et al. | |
| 8,641,724 B2 | 2/2014 | Brenneman et al. | |
| 8,926,545 B2 | 1/2015 | Brenneman et al. | |
| 2003/0014061 A1 | 1/2003 | Houser et al. | |
| 2004/0249335 A1 * | 12/2004 | Faul | A61B 17/11 604/9 |
| 2005/0075656 A1 | 4/2005 | Beaupre | |
| 2005/0277965 A1 | 12/2005 | Brenneman et al. | |
| 2005/0278013 A1 | 12/2005 | Rust et al. | |
| 2008/0109069 A1 * | 5/2008 | Coleman | A61B 17/11 623/1.25 |
| 2009/0163847 A1 * | 6/2009 | Kapadia | A61F 2/06 604/8 |
| 2010/0268316 A1 | 10/2010 | Brenneman et al. | |
| 2011/0184504 A1 | 7/2011 | Ward et al. | |
| 2011/0213459 A1 * | 9/2011 | Garrison | A61F 2/013 623/2.11 |
| 2011/0251482 A1 | 10/2011 | Kellerman et al. | |
| 2011/0270149 A1 | 11/2011 | Faul et al. | |

OTHER PUBLICATIONS

International search report and written opinion dated May 23, 2014 for PCT/US2013/011912.

European Search Report dated Aug. 25, 2016 for International Application No. 14742861.9.

International Search Report and Written Opinion dated May 23, 2014 for International PCT Patent Application No. PCT/US2014/011912.

* cited by examiner

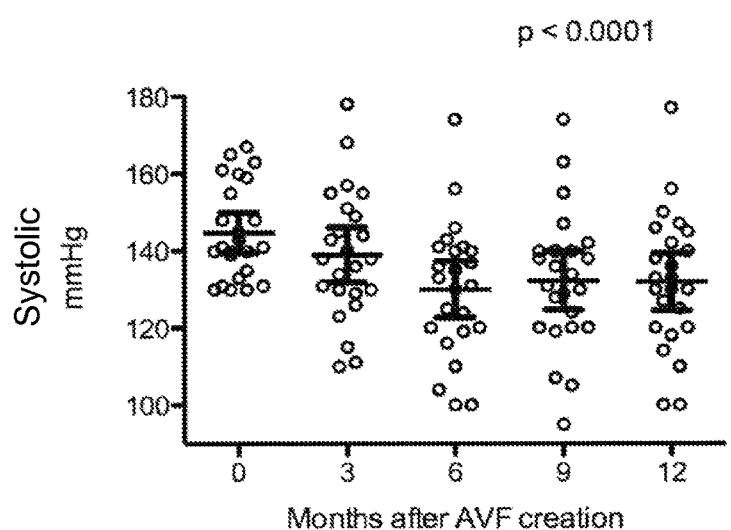

FIG 3E

Systolic blood pressure recordings at baseline (0) and at 3, 6, 9, and 12 months after creation of an iliac arteriovenous anastomosis using an anastomotic coupler device (Rox Medical, San Clemente, CA) ($p<0.0001$, by ANOVA). Means and 95% Confidence Intervals at each time point are indicated by error bars. Post analysis testing revealed a differences between baseline and 3 months, baseline and 6 months, baseline and 9 months, baseline and 12 months, and between 3 months and 12 months.

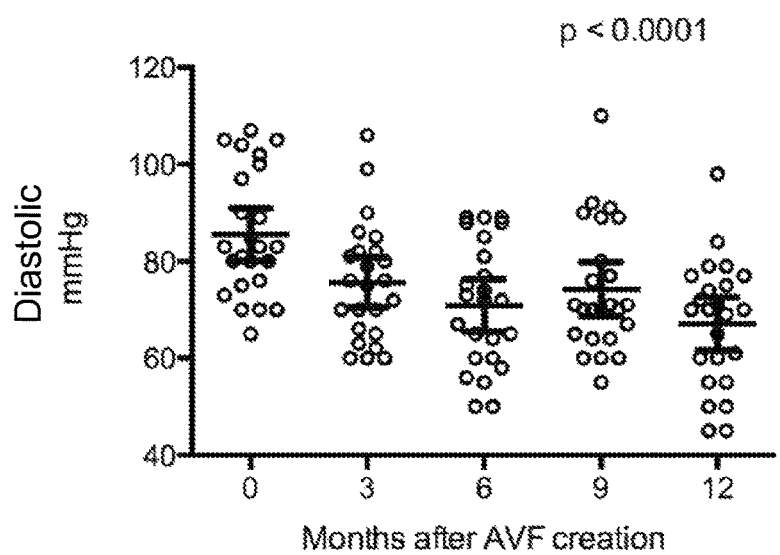

FIG 3F

Diastolic blood pressure recordings at baseline (0) and 3, 6, 9, and 12 months after creation of an iliac arteriovenous anastomosis using an anastomotic coupler device (Rox Medical, San Clemente, CA) (p<0.0001, by ANOVA). Means and 95% Confidence Intervals at each time point are indicated by error bars. Post analysis testing revealed significant differences between baseline and 6 months, baseline and 9 months, and baseline and 12 months.

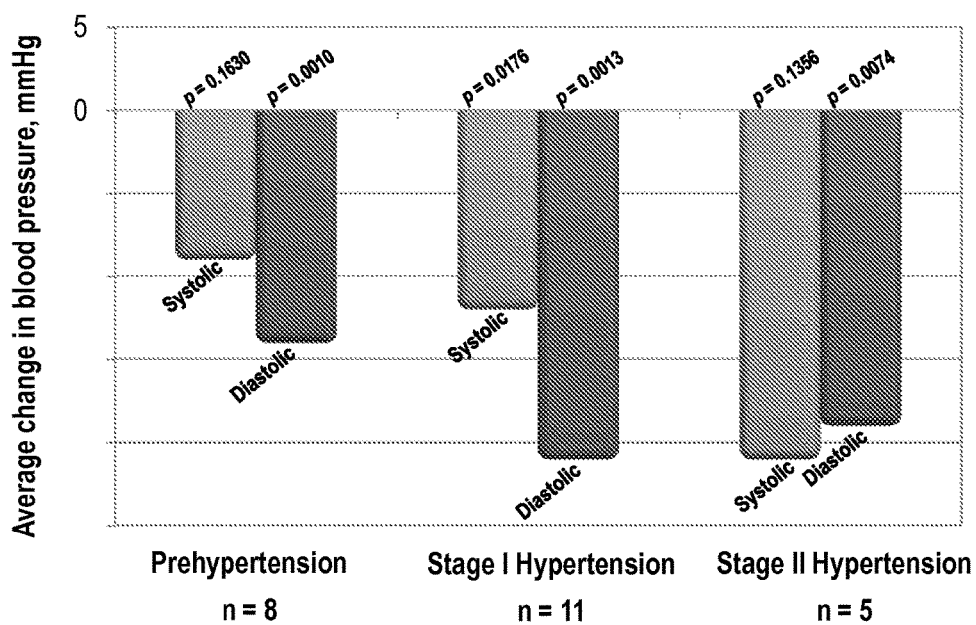

FIG 4

Histogram of the change in clinic based systolic and diastolic blood pressure measurements at 12 months according to stage of hypertension: pre-hypertension subjects (n = 8) had a baseline systolic blood pressure between 130 mmHg and 139 mmHg, Stage I hypertension subjects had baseline systolic blood pressure between 140 mmHg and 159 mmHg (n = 11), and Stage II hypertension subjects had a baseline systolic blood pressure greater than or equal to 160 mmHg (n = 5). At 12 months the reductions in systolic blood pressure recordings were 9 mmHg (p = ns), 12 mmHg (p = 0.02), and 21 mmHg (p = ns), respectively, while the changes in diastolic blood pressure recordings were 14 mmHg (p = 0.001), 21 mmHg (p = 0.001), and 19 mmHg (p = 0.01), respectively.

METHODS, SYSTEMS AND DEVICES FOR TREATING CARDIAC ARRHYTHMIAS

CROSS-REFERENCE TO RELATED APPLICATIONS

This application claims priority to U.S. Provisional Application No. 61/755,789, filed Jan. 23, 2013, the entire contents of which are incorporated herein by reference.

This application is related to, but does not claim priority to, the following applications: U.S. Pat. No. 7,828,814, entitled "Device and Method for Establishing an Artificial Arterio-Venous Fistula", filed Apr. 4, 2007; U.S. Non-Provisional application Ser. No. 11/152,621, entitled "Devices for Arterio-Venous Fistula Creation", filed Jun. 13, 2005; U.S. Non-Provisional application Ser. No. 11/151,802, entitled "Methods for Providing Oxygenated blood to Venous Circulation", filed Jun. 13, 2005; U.S. Non-Provisional application Ser. No. 11/946,454, entitled "Devices, Systems, and Methods for Creation of a Peripherally Located Fistula", filed Nov. 28, 2007; U.S. Non-Provisional application Ser. No. 12/017,437, entitled "Devices, Systems, and Methods for Peripheral Arteriovenous Fistula Creation", filed Jan. 22, 2008; U.S. Non-Provisional application Ser. No. 12/752,397, entitled "Device and Method for Establishing an Artificial Arteriovenous Fistula", filed Apr. 1, 2010; U.S. Non-Provisional application Ser. No. 12/905,412, entitled "Devices, Systems, and Methods for Enhanced Visualization of the Anatomy of a Patient", filed Oct. 15, 2010; and PCT Application Number PCT/US2013/62458, entitled "Methods, Systems and Devices for Treating Hypertension", filed Sep. 27, 2013; the contents of each are incorporated herein by reference in their entirety.

TECHNICAL FIELD

The embodiments disclosed herein relate generally to systems, devices and methods for treating a patient, particularly a patient afflicted with a cardiac arrhythmia or compromised cardiac structure.

BACKGROUND

Cardiac dysrhythmia (also known as arrhythmia or irregular heartbeat) is any of a large and heterogeneous group of conditions in which there is abnormal electrical activity in the heart. The heartbeat may be too fast or too slow, and may be regular or irregular. A heart beat that is too fast is called tachycardia and a heart beat that is too slow is called bradycardia.

Some arrhythmias are life-threatening medical emergencies that can result in cardiac arrest. In fact, cardiac arrythmias are one of the most common causes of death when travelling to a hospital. Others cause symptoms such as an abnormal awareness of heart beat (palpitations), and may be merely uncomfortable. These palpitations have also been known to be caused by atrial/ventricular fibrillation, wire faults, and other technical or mechanical issues in cardiac pacemakers/defibrillators. Still others may not be associated with any symptoms at all, but may predispose the patient to potentially life threatening stroke or embolism.

The term sinus arrhythmia refers to a normal phenomenon of mild acceleration and slowing of the heart rate that occurs with breathing in and out. It is usually quite pronounced in children, and steadily decreases with age. This can also be present during meditation breathing exercises that involve deep inhaling and breath holding patterns. Proarrhythmia is a new or more frequent occurrence of pre-existing arrhythmias, paradoxically precipitated by antiarrhythmic therapy, which means it is a side effect associated with the administration of some existing antiarrhythmic drugs, as well as drugs for other indications. In other words, it is a tendency of antiarrhythmic drugs to facilitate emergence of new arrhythmias.

Current treatment methods, such as the administration of pharmaceuticals, cardiac stimulators and cardiac ablation therapy, are associated with incomplete or otherwise limited treatment; high cost; invasiveness; and numerous undesirable side effects. There is therefore a need for improved approaches, including both devices and methods, for treating patients suffering from cardiac arrhythmia or compromised cardiac function.

SUMMARY

According to one aspect, a method for treating a patient comprises selecting a patient for treatment and creating a flow pathway between a first vascular location and a second vascular location, wherein the method is constructed and arranged to provide at least one of a therapeutic treatment of a cardiac arrhythmia or an improvement of a function of a cardiac structure.

The patient can exhibit an arterial blood pressure greater than 180 mmHg prior to creation of the flow pathway. The patient can exhibit an arterial blood pressure between 160 mmHg and 180 mmHg prior to creation of the flow pathway. The patient can exhibit an arterial blood pressure between 130 mmHg and 160 mmHg prior to creation of the flow pathway. The patient can have been diagnosed with renal artery calcification and/or compromised kidney function such as kidney failure.

The first vascular location can comprise a source of arterial blood. For example, the first vascular location can comprise an artery selected from the group consisting of: aorta; axillary; brachial; ulnar; radial; profundal; femoral; iliac; popliteal; and carotid. The second vascular location can comprise a source of venous blood. For example, the second vascular location can comprise a vein selected from the group consisting of: inferior vena cava; saphenous; femoral; iliac; popliteal; brachial; basilic; cephalic; medial forearm; medial cubital; axillary; and jugular.

The flow pathway can comprise a fistula. The flow pathway can comprise an anastomosis. The flow pathway can comprise an anatomical location relatively proximate to a kidney of the patient. The flow pathway can comprise an anatomical location positioned at a location that comprises an infrarenal and/or a supra-renal anatomical location, for example when the first vascular location comprises an artery.

The first vascular location can comprise a chamber of the heart. In some embodiments, the first vascular location comprises the left atrium and the second vascular location comprises the right atrium. In some embodiments, the first vascular location comprises the left ventricle and the second vascular location comprises the coronary sinus.

The first vascular location can comprise the aorta and the second vascular location can comprise a vein, and the flow pathway can comprise a graft positioned between the aorta and the vein.

The flow pathway can comprise an average cross sectional area of less than 20 mm$^2$, for example an average cross sectional area of less than 12.6 mm$^2$, or an average cross sectional area of less than 9.7 mm$^2$, or an average cross sectional area of less than 7.1 mm$^2$.

The average cross sectional area of the flow pathway can be selected based on a patient parameter such as a patient blood pressure parameter. For example, the flow pathway average cross sectional area can be proportionally related to the patient blood pressure parameter.

In cases where the cardiac arrhythmia treated comprises atrial fibrillation, the method can reduce atrial fibrillation occurrence. The method can provide a therapeutic treatment for a patient disease selected from the group consisting of: chronic atrial fibrillation; persistent atrial fibrillation; paroxysmal atrial fibrillation; and combinations of these. Treating the cardiac arrhythmia can comprise reducing systemic arterial pressure. Other examples of the cardiac arrhythmia treated can include: ventricular tachycardia; right atrial flutter; atrial fibrillation; and combinations of these.

The method can improve a function of a cardiac structure to treat valve regurgitation, for example a valve selected from the group consisting of: mitral valve; aortic valve; and combinations of these.

The method can treat a patient condition selected from the group consisting of: valve regurgitation; valve insufficiency; chronic high left heart pressures; and combinations of these.

The method can be further constructed and arranged to reduce central sympathetic neural activity. The method can be further constructed and arranged to reduce a patient parameter selected from the group consisting of: peripheral vascular resistance; left ventricular pre-load; left ventricular pressure; left atrial volume; left atrial volume; left atrial stretching; and combinations of these. The method can be further constructed and arranged to reduce the likelihood of blood clot formation. The method can be further constructed and arranged to provide a treatment for systemic arterial hypertension, for example where the method provides a treatment for drug-resistant hypertension. The method can be further constructed and arranged to reduce diastolic blood pressure and/or systolic blood pressure, for example where the reduction in diastolic blood pressure and the reduction in systolic blood pressure are relatively equivalent in magnitude.

The method can be constructed and arranged to provide an increase to the compliance of the arterial vascular system, for example where the method causes a release of at least one of chemo-receptors or a vaso-dilating factor. The flow pathway can be created based on a measurement of at least one of vascular tone or vascular compliance.

The method can be constructed and arranged to lower blood pressure within a patient organ, for example an organ selected from the group consisting of: liver; kidney; heart; brain; and combinations of these.

The method can be further constructed and arranged to treat a patient disease or disorder selected from the group consisting of: chronic obstructive pulmonary disease; congestive heart failure; lung fibrosis; adult respiratory distress syndrome; lymphangioleiomytosis; pulmonary hypertension; sleep apnea such as sleep apnea due to hypoxemia or hypertension; and combinations of these.

The method can further comprise performing a second treatment on the patient.

The second treatment can comprise administering a pharmaceutical agent to the patient, for example an agent selected from the group consisting of: anti-arrhythmia drug; anti-thrombotic agent; and combinations of these.

The second treatment can comprise performing the Cox-Maze procedure on the patient.

The second treatment can comprise a performing a cardiac ablation procedure on the patient. The cardiac ablation procedure can comprise a surgical ablation procedure. The ablation procedure can be performed with interventional catheter devices. The cardiac ablation procedure can comprise at least a pulmonary vein isolation ablation procedure. The cardiac ablation procedure can comprise a cardiac ablation procedure selected from the group consisting of: ablation to isolate one or more pulmonary veins; ablation of the left atrial posterior wall; ablation of the left atrial septum; and combinations of these. The cardiac ablation procedure can comprise delivery of energy to cardiac tissue wherein the energy delivered is selected from the group consisting of: radiofrequency energy; laser energy; ultrasound energy; chemical energy; and combinations of these.

The second treatment can comprise treating a heart valve, for example a valvuloplasty procedure.

The second treatment can comprise a renal denervation procedure. The renal denervation procedure can be performed in the same clinical procedure in which the flow pathway is created. The renal denervation procedure can be performed prior to and/or after the clinical procedure in which the flow pathway is created. The flow pathway can be created based on a blood pressure reduction caused by the renal denervation procedure, for example where the blood pressure reduction comprises a reduction in at least one of systolic blood pressure or diastolic blood pressure.

The second treatment can comprise placing a stent in a renal vessel.

The second treatment can comprise dilating a renal vessel.

The flow pathway can be created in a clinical procedure and the second treatment can be performed in the same clinical procedure in which the flow pathway is created. The second treatment can be performed within twenty four hours of creation of the flow pathway. The second procedure can be performed in a previous clinical procedure than the clinical procedure in which the flow pathway is created, for example at least one week prior to the clinical procedure in which the flow pathway is created, or at least six months prior to the clinical procedure in which the flow pathway is created. The second procedure can be performed in a subsequent clinical procedure than the clinical procedure in which the flow pathway is created, for example at least one week after the clinical procedure in which the flow pathway is created, or at least six months after the clinical procedure in which the flow pathway is created.

The method can further comprise performing a diagnostic procedure to produce diagnostic data. The diagnostic data can comprise patient diagnostic data. The creation of the flow pathway can be performed based on the diagnostic data. The diagnostic data can comprise blood pressure data, for example where the blood pressure data is obtained over a period of at least sixty minutes.

The flow pathway can comprise an average cross sectional area, and the average cross sectional area can be based on the diagnostic data. The diagnostic data can comprise blood pressure data, for example where the blood pressure data is obtained over a period of at least sixty minutes.

The diagnostic procedure can produce patient diagnostic data selected from the group consisting of: central blood pressure data; vascular tone data; central sympathetic tone data; cardiac output data; peripheral vascular resistance data; and combinations of these.

The method can be constructed and arranged to cause a decrease in vascular resistance, for example a decrease in peripheral vascular resistance such as infrarenal vascular resistance.

The method can be further constructed and arranged to cause a physiologic change in the patient selected from the group consisting of: increased oxygen delivery by the arterial system; increased blood volume; increased proportion of blood flow to the descending aorta; increased blood flow to the kidneys; increased blood flow outside the kidneys; increased cardiac output; and combinations of these.

The method can be further constructed and arranged to minimize chronic increase in heart rate.

The method can be further constructed and arranged to minimize a decrease in cardiac function.

The method can be further constructed and arranged to minimize adverse effects to a kidney of the patient.

The method can be further constructed and arranged to cause at least one of an increase in oxygenation or an increase in flow rates associated with the patient's chemoreceptors.

The method can be further constructed and arranged to modify the patient's central sympathetic tone. For example, the modification to the patient's central sympathetic tone can cause a reduction in at least one of systolic or diastolic blood pressure. Additionally or alternatively, the modification to the patient's central sympathetic tone can provide a therapeutic benefit to a patient disease or disorder selected from the group consisting of: diabetes; sleep apnea; heart failure; and combinations of these.

The method can further comprise dilating the flow pathway. The dilation can be performed by inflating a balloon in the flow pathway. The dilation can be performed at a diameter between 3 mm and 5 mm, for example at a diameter of approximately 4 mm.

The method can further comprise performing a flow pathway assessment procedure. The flow pathway assessment procedure can comprise performing an anatomical measurement, for example a measurement selected from the group consisting of: a flow pathway diameter measurement; a flow pathway length measurement; a measurement of the distance between an artery and vein comprising the flow pathway; a measurement of the distance between the flow pathway and a vessel sidebranch; and combinations of these. The flow pathway assessment procedure can comprise performing an assessment of at least one of flow in the flow pathway or flow proximate the flow pathway, for example a flow assessment selected from the group consisting of: flow through the flow pathway; flow in a vessel segment proximate the flow pathway; flow measured using Doppler Ultrasound; flow measured using angiographic techniques; and combinations of these. The flow pathway assessment procedure can comprise an assessment of a patient physiologic condition, for example a condition selected from the group consisting of: cardiac output; blood pressure such as systolic and/or diastolic blood pressure; respiration; a blood gas parameter; blood flow; vascular resistance; pulmonary resistance; an average clotting time assessment; serum creatinine level assessment; and combinations of these.

The method can further comprise placing an implant in the flow pathway. The implant can comprise an anastomotic clip. The implant can comprise an implant selected from the group consisting of: suture; staple; adhesive; and combinations of these. The implant can comprise at least a portion that comprises biodegradable material.

The method can further comprise modifying the flow pathway. Modifying the flow pathway can comprise dilating at least a portion of the flow pathway. The method can further comprise placing an anastomotic clip in the flow pathway, and the modifying the flow pathway can be performed after the placement of the anastomotic clip. Modification of the flow pathway can be performed at least one week after the creating of the flow pathway. Modifying the flow pathway can comprise modifying a flow parameter selected from the group consisting of: flow pathway cross sectional diameter; flow pathway average cross sectional diameter; flow pathway flow rate; flow pathway average flow rate; diastolic pressure after flow pathway creation; diastolic pressure change after flow pathway creation (e.g. as compared to diastolic pressure prior to flow pathway creation); systolic pressure after flow pathway creation; systolic pressure change after flow pathway creation (e.g. as compared to systolic pressure prior to flow pathway creation); ratio of diastolic to systolic pressure after flow pathway creation; difference between diastolic pressure and systolic pressure after flow pathway creation; and combinations of these. Modifying the flow pathway comprises a flow modification procedure selected from the group consisting of: increasing flow through the flow pathway; decreasing flow through the flow pathway; increasing the diameter of at least a segment of the flow pathway; decreasing the diameter of at least a segment of the flow pathway; removing tissue proximate the flow pathway; blocking a sidebranch proximate the flow pathway; and combinations of these.

The method can further comprise creating a second flow pathway between a third vascular location and a fourth vascular location. The first vascular location can comprise an artery and the third vascular location can comprise the same artery. The second vascular location can comprise a vein and the fourth vascular location can comprise the same vein. The second flow pathway can comprise a fistula. The second flow pathway can be created at least twenty four hours after the creation of the first flow pathway. The method can further comprise occluding the first flow pathway.

According to another aspect, a system is constructed and arranged to create and maintain the flow pathway of the method described above. The system can further comprise an algorithm for determining average fistula cross sectional area, for example based on a patient parameter such as a patient blood pressure parameter.

According to another aspect, a system for treating a patient comprises a needle delivery device constructed and arranged to place a vessel-to-vessel guidewire from a first vascular location to a second vascular location and a flow creation device constructed and arranged to be advanced over the vessel-to-vessel guidewire and to create a flow pathway between the first vascular location and the second vascular location, wherein the system is constructed and arranged to treat a cardiac arrhythmia.

The cardiac arrhythmia can comprise atrial fibrillation.

The system can further comprise an algorithm for determining average fistula cross sectional area, for example based on a patient parameter such as a patient blood pressure parameter.

The system can be further constructed and arranged to cause a reduction in systolic blood pressure.

The system can be further constructed and arranged to cause a reduction in diastolic pressure to an extent at least approximating a reduction in systolic pressure, or an extent greater than a reduction in systolic pressure.

The needle delivery device can comprise an advanceable needle. The needle delivery device can comprise a needle with a gauge between 20 and 24, for example an approximately 22 gauge needle. The needle delivery device can comprise a curved needle. The needle delivery device can further comprise a marker indicating the direction of curvature of the curved needle, for example a marker selected from the group consisting of: flat surface, visible marker, line, textured surface, and combinations of these. The needle delivery device can further comprise a sheath constructed and arranged to slidingly receive the curved needle. The needle can comprise a proximal end and a hub positioned on said proximal end, and the hub can be constructed and arranged to be advanced to advance the curved needle out of the sheath. The needle delivery device can comprise a needle comprising a shaped memory alloy, for example nickel titanium alloy.

The system can further comprise a vessel-to-vessel guidewire constructed and arranged to be placed from the first vascular location to the second vascular location by the needle delivery device. The vessel-to-vessel guidewire can comprise a wire with an outer diameter approximating 0.018". The vessel-to-vessel guidewire can comprise a marker, for example marker positioned to indicate the fistula location. The vessel-to-vessel guidewire can comprise a distal portion and a mid portion where the mid portion can comprise a construction different than the construction of the distal portion, for example where the mid portion comprises a stiffness greater than the stiffness of the distal portion.

The flow creation device can comprise a balloon catheter configured to dilate tissue positioned between the first vascular location and the second vascular location.

The flow creation device can comprise an energy delivery device constructed and arranged to deliver energy to tissue positioned between the first vascular location and the second vascular location.

The flow creation device can comprise a clip deployment catheter comprising an anastomotic clip. The clip deployment catheter can comprise a handle and the handle can comprise a control constructed and arranged to deploy the anastomotic clip. The control can comprise a button. The handle can comprise a safety position for the control. The handle can comprise a longitudinal axis, and the control can be constructed and arranged to be moved relatively perpendicular to said longitudinal axis to transition from the safety position to a first ready to deploy position. The clip can comprise at least two distal arms, and the handle can be constructed and arranged to allow an operator to move the control from a first ready to deploy position to a first deployed position, where the movement causes the at least two distal arms to be deployed. The handle can comprise a longitudinal axis and the control can be moved relatively parallel to said longitudinal axis to transition from the first ready to deploy position to the first deployed position. The handle can be constructed and arranged to allow an operator to move the control from the first deployed position to a second ready to deploy position, for example, the control can be moved relatively perpendicular to the longitudinal axis to transition from the first deployed position to the second ready to deploy position. The clip can comprise at least two proximal arms, and the handle can be constructed and arranged to allow an operator to move the control from the second ready to deploy position to a second deployed position, where the movement causes the at least two proximal arms to be deployed. The control can be moved relatively parallel to said longitudinal axis to transition from the second ready to deploy position to the second deployed position.

The clip deployment catheter can comprise an outer sheath and the control can be constructed and arranged to be moved from a first position to a second position to cause movement of the outer sheath. The clip deployment catheter can be constructed and arranged such that movement of the control to the second position causes a tactile feedback event to occur. The clip can comprise multiple deployable arms, and the clip deployment catheter can be constructed and arranged such that movement of the control to the second position causes at least one arm to be deployed.

At least one of the clip deployment catheter or the clip can comprise at least one marker constructed and arranged to rotationally position the clip. The marker can be constructed and arranged to be oriented toward the target vessel prior to deployment of the clip, for example where the marker is oriented based on a patient image such as a real-time fluoroscopy image. The clip can comprise a swing arm for deployment in the second vascular location and the marker can be positioned in alignment with the swing arm. The marker can be positioned on the clip. The clip deployment catheter can comprise a distal portion and said distal portion can comprise the clip and the marker, for example where the marker is positioned proximate the clip. The clip deployment catheter can comprise a proximal portion and said proximal portion can comprise the marker, for example where the clip deployment catheter comprises a handle and the marker is positioned on the handle.

At least one of the clip deployment catheter or the clip can comprise at least one marker constructed and arranged to longitudinally position the clip at the fistula location, for example where the marker indicates a distal end and/or a proximal end of the clip.

The clip can comprise multiple deployable arms, and the clip deployment catheter can be constructed and arranged to deploy at least one of said deployable arms and subsequently recapture said one of said deployable arms.

The clip deployment catheter can be constructed and arranged to be rotated and simultaneously deployed from the first vascular location to the second vascular location over the vessel-to-vessel guidewire.

The clip deployment catheter can comprise a projection constructed and arranged to mechanically engage the clip. The projection can comprise a pin. The clip deployment catheter can further comprise a second projection constructed and arranged to mechanically engage the clip.

The system can further comprise a flow pathway maintaining implant. The flow pathway maintaining implant can comprise an anastomotic clip. The clip can comprise a plurality of distal arms and a plurality of proximal arms where the distal arms are independently deployable from the proximal arms. The clip can comprise four deployable distal arms and/or four deployable proximal arms. The clip can comprise nickel titanium alloy. The clip can comprise multiple deployable arms and at least two arms can comprise a marker, for example a radiopaque marker.

The flow pathway maintaining implant can comprise suture; one or more staples; adhesive; at least a portion that comprises biodegradable material; and combinations of these.

The system can further comprise a venous system introducer. The venous system introducer can be constructed and arranged to access the first vascular location. The venous system introducer can comprise an 11 French introducer. The venous system introducer can comprise a beveled tip comprising an angle between 20° and 50°, for example an angle of approximately 30°. The venous system introducer can comprise a marker proximate the beveled distal tip, for example a radiopaque marker. The venous system introducer can comprise a proximal portion comprising a marker, where the marker is aligned with the beveled distal tip. The venous system introducer can comprise a distal portion and an expandable element mounted to the distal portion. The expandable element can comprise a balloon. The expandable element can be constructed and arranged to prevent inadvertent advancement of the introducer into the second vascular location. The venous system introducer can be constructed and arranged to stabilize the first vascular location.

The system can further comprise an arterial system introducer. The arterial system introducer can be constructed and arranged to access the second vascular location. The arterial system introducer can comprise a 4 French introducer.

The system can further comprise a target wire constructed and arranged for positioning in the second vascular location. The target wire can comprise a helical distal portion and/or a radiopaque distal portion.

The system can further comprise a flow pathway modifying device. The flow pathway modifying device can comprise an expandable element. The expandable element can be constructed and arranged to expand to a diameter between 3 mm and 5 mm, for example a diameter of approximately 4 mm. The expandable element can comprise a balloon. The expandable element can comprise at least one of an expandable cage or radially deployable arms.

The flow modifying device can comprise a device selected from the group consisting of: an over the wire device constructed and arranged to be delivered over a vessel-to-vessel guidewire; an expanding scaffold configured to increase or otherwise modify flow pathway geometry such as an expandable balloon; an energy delivery catheter such as a catheter configured to deliver energy to tissue proximate a flow pathway; an agent delivery catheter such as a catheter configured to deliver an agent such as a pharmaceutical agent or an adhesive such as fibrin glue; and combinations of these.

The system can further comprise a patient imaging apparatus. For example, the patient imaging apparatus can include a fluoroscope and/or an ultrasound imager.

The system can be further constructed and arranged to treat a patient disease or disorder selected from the group consisting of: chronic obstructive pulmonary disease; congestive heart failure; lung fibrosis; adult respiratory distress syndrome; lymphangioleiomytosis; pulmonary hypertension; sleep apnea such as sleep apnea due to hypoxemia or hypertension; and combinations of these.

According to another aspect, a system for creating a fistula between a first vascular location and a second vascular location at a fistula location in a patient comprises a vascular introducer; a needle delivery device; a vessel-to-vessel guidewire constructed and arranged to be placed from the first vascular location to the second vascular location by the needle delivery device; an anastomotic clip; and a clip deployment catheter constructed and arranged to deploy the anastomotic clip.

The system can be constructed and arranged to treat atrial fibrillation. The system can be constructed and arranged to treat a patient disease or disorder selected from the group consisting of: cardiac arrhythmia; chronic obstructive pulmonary disease; congestive heart failure; lung fibrosis; adult respiratory distress syndrome; lymphangioleiomytosis; pulmonary hypertension; sleep apnea such as sleep apnea due to hypoxemia or hypertension; and combinations of these.

BRIEF DESCRIPTION OF THE DRAWINGS

The accompanying drawings, which are incorporated in and constitute a part of this specification, illustrate various embodiments of the present inventive concepts, and, together with the description, serve to explain the principles of the invention. In the drawings:

FIGS. 3E and 3F are graphs of blood pressure measurements recorded from patients receiving a flow pathway, consistent with the present inventive concepts.

FIG. 4 is a table of average change in blood pressure recorded from patients receiving a flow pathway, consistent with the present inventive concepts.

FIGS. 6A, 6B and 6C are anatomical views of three different needle trajectory paths, consistent with the present inventive concepts.

DETAILED DESCRIPTION OF THE DRAWINGS

Figure 1:
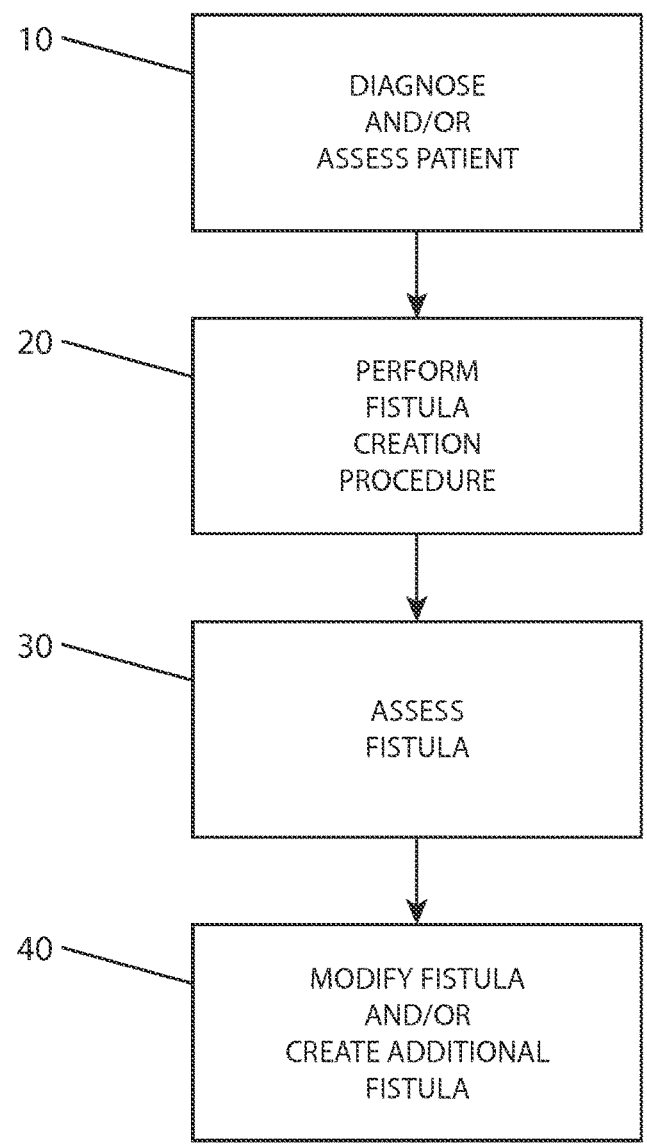
FIG. 1 is a flow chart of a method for treating a patient by creating a flow pathway between a first vascular location and a second vascular location, consistent with the present inventive concepts.

Reference will now be made in detail to the present embodiments of the inventive concepts, examples of which are illustrated in the accompanying drawings. Wherever practical, the same reference numbers will be used throughout the drawings to refer to the same or like parts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Referring now to FIG. 1, a flow chart for selecting and treating a patient by creating a fistula or other flow pathway (hereinafter "fistula") between a first vascular location in the patient's arterial system and a second vascular location in the patient's venous system is illustrated, consistent with the present inventive concepts. In STEP 10, a patient assessment is performed, such as to diagnose the patient and determine if a fistula should be created in the patient. A patient can be selected based on a disease or disorder which is diagnosed in STEP 10 or previously. In some embodiments, a patient diagnosed with a cardiac arrhythmia and/or a compromised cardiac structure is selected to receive a fistula. Alternatively or additionally, a patient selected to receive a fistula can have a disease or disorder selected from the group consisting of: hypertension; chronic obstructive pulmonary disease (COPD); congestive heart failure; lung fibrosis; adult respiratory distress syndrome; lymphangioleiomytosis; pulmonary hypertension; sleep apnea such as sleep apnea due to hypoxemia or hypertension; and combinations of these.

In some embodiments, the patient is selected for fistula creation of the present inventive concepts based on the presence of a cardiac arrhythmia such as atrial fibrillation, such as chronic, persistent and/or paroxysmal atrial fibrillation. In some embodiments, the fistula is created to reduce recurrence of atrial fibrillation. In some embodiments, the fistula is created to reduce systemic arterial pressure to treat a cardiac arrhythmia, such as to cause a reduction in atrial fibrillation events. In some embodiments, the patient is selected to receive a fistula based on the presence of a cardiac arrhythmia selected from the group consisting of: ventricular tachycardia; right atrial flutter; atrial fibrillation; and combinations of these.

In some embodiments, the patient is selected for fistula creation of the present inventive concepts based on the presence of a compromised cardiac structure, such as a cardiac structure related to a patient disease or disorder selected from the group consisting of: valve regurgitation; valve insufficiency; chronic high left heart pressures; and combinations of these. In some embodiments, the compromised cardiac structure is associated with regurgitation of the mitral and/or aortic valve.

In some embodiments, the patient is selected for fistula creation of the present inventive concepts based on exhibiting an arterial blood pressure greater than 180 mmHg. In other embodiments, the patient is selected for fistula creation based on exhibiting an arterial blood pressure between 130 mmHg and 180 mmHg, such as a range between 130 mmHg and 160 mmHg or a range between 160 mmHg and 180 mmHg. In some embodiments, a patient is selected for fistula creation if calcification in the renal artery is present. In some embodiments, a patient is selected for fistula creation if compromised kidney function is present, such as the presence of kidney failure.

In STEP 10, one or more diagnostic procedures can be performed to produce diagnostic data, such as patient physiologic data or other patient data. The fistula created in STEP 20 described herebelow may be sized, formed or otherwise based on the diagnostic data. The optional fistula modification step described in STEP 40 herebelow may be based on the diagnostic data. Additional diagnostic procedures can be performed in any of STEPS 10 through 40.

In STEP 20, a fistula creation procedure is performed on the patient. In some embodiments, the fistula creation procedure is performed as described in reference to FIG. 5 herebelow. In some embodiments, the fistula creation procedure is performed using a system of devices and components similar to system 100 of FIG. 2 described herebelow. The fistula or other flow pathway creation system used can include an algorithm used to create the fistula such as an algorithm using a patient parameter (e.g. blood pressure) to determine a fistula parameter such as fistula cross sectional area. The fistula is created between a first vascular location in the arterial system, such as an artery, and a second vascular location in the venous system, such as a vein. The fistula creation procedure can include the placement of a vessel-to-vessel guidewire between a starting vessel such as a vein, and a target vessel such as an artery. In these embodiments, the fistula can be created using one or more fistula creation devices that are advanced over the vessel-to-vessel guidewire. An anastomotic clip or other implant can be placed into the fistula via a clip placement device advanced over the vessel-to-vessel guidewire. Alternatively, a fistula can be created without an anastomotic clip, such as through the use of energy (e.g. radiofrequency energy), suture or staple (e.g. via an over-the-wire suture or staple delivery device used to create an anastomosis at either or both ends of the fistula), and/or a tissue treatment such as an adhesive (e.g. fibrin glue) coating of the tissue surrounding or otherwise proximate the fistula. One or more fistula treatment or modification procedures can be performed using fistula treatment or modification devices advanced over the vessel-to-vessel guidewire, such as a fistula modification performed in STEP 40 herebelow.

In some embodiments, a fistula is created between an artery and a vein at a location distal to the renal arteries (i.e. an infrarenal location). Alternatively or additionally, a fistula can be created between an artery and a vein at a location proximal to the renal arteries (i.e. a suprarenal location). In some embodiments, a fistula is created proximate a kidney. Numerous locations for the fistula can be selected, such as a fistula located between an artery and vein as described in reference to FIG. 5 herebelow. Alternatively or additionally, a fistula can be created between a chamber of the heart and a second vascular location, such as between the left atrium and the right atrium or between the left ventricle and the heart's coronary sinus. Alternatively or additionally, arterial blood can be diverted to the venous system by way of a fistula comprising an anastomosed bypass graft, such as is described in applicant's issued patent U.S. Non-Provisional application Ser. No. 11/151,802, entitled "Methods for Providing Oxygenated Blood to Venous Circulation", filed Jun. 13, 2005, the contents of which are incorporated by reference herein in its entirety.

During the fistula creation procedure and/or in a subsequent fistula modification procedure, a fistula dilation procedure can be performed. In some embodiments, an anastomotic clip is placed in the fistula and a balloon catheter is used to dilate the fistula and anastomotic clip simultaneously. In some embodiments, the balloon comprises a diameter of approximately 3 mm to 5 mm, such as a diameter of approximately 4 mm. In some embodiments, the fistula is created and/or modified to comprise an average cross sectional area of less than 20 mm$^2$, such as a cross sectional area less than 12.6 mm$^2$, less than 9.7 mm$^2$, or less than 7.1 mm$^2$. In some embodiments, the fistula is created and/or modified to have a cross sectional area based on the patient's blood pressure, such as a cross sectional area that is proportionally related to the patient's blood pressure (i.e. the higher the blood pressure the larger the cross sectional area).

In STEP 30, a fistula assessment procedure can be performed. One or more diagnostic procedures can be performed to produce diagnostic data as described in reference to STEP 10 hereabove. STEP 30 can be performed in the same clinical procedure as STEP 20, and/or in a subsequent clinical procedure such as a procedure at least twenty-four hours after completion of STEP 20, or at least 1 week, at least 1 month, and/or at least 6 months after completion of STEP 20. In some embodiments, the assessment performed in STEP 30 includes one or more anatomical measurements, such as a measurement selected from the group consisting of: a fistula diameter measurement; a fistula length measurement; a measurement of the distance between the artery and vein comprising the fistula; a measurement of the distance between the fistula and a vessel sidebranch; and combinations of these. In some embodiments, the assessment performed in STEP 30 comprises an assessment of flow, such as a flow assessment selected from the group consisting of: flow through the fistula; flow in a vessel segment proximate the fistula; flow measured using Doppler Ultrasound; flow measured using angiographic techniques; and combinations of these. In some embodiments, the assessment performed in STEP 30 comprises an assessment of a patient physiologic condition, such as an assessment of a physiologic condition selected from the group consisting of: cardiac output; blood pressure such as systolic and/or diastolic blood pressure; respiration; a blood gas parameter; blood flow; vascular resistance; pulmonary resistance; an average clotting time assessment; serum creatinine level assessment; and combinations of these.

In STEP 40, one or more fistula parameters can be modified and/or a second clinical procedure can be performed (e.g. the creation of a second fistula at a different anatomical location). STEP 40 can be performed in the same clinical procedure as STEP 20, and/or in a subsequent clinical procedure such as a procedure at least twenty-four hours after completion of STEP 20, or at least 1 week, at least 1 month, and/or at least 6 months after completion of STEP 20. In some embodiments, STEP 30 and STEP 40 are performed in the same clinical procedure (e.g. both in the same clinical procedure as STEP 20 or both in a subsequent clinical procedure). In some embodiments, one or more patient or fistula parameters to be modified are selected from the group consisting of: fistula cross sectional diameter; fistula average cross sectional diameter; fistula flow rate; fistula average flow rate; diastolic pressure after fistula creation; diastolic pressure change after fistula creation (e.g. as compared to diastolic pressure prior to fistula creation); systolic pressure after fistula creation; systolic pressure change after fistula creation (e.g. as compared to systolic pressure prior to fistula creation); ratio of diastolic to systolic pressure after fistula creation; difference between diastolic pressure and systolic pressure after fistula creation; and combinations of these.

Fistula modification procedures can include but are not limited to: increasing flow through the fistula; decreasing flow through the fistula; increasing the diameter of at least a segment of the fistula; decreasing the diameter of at least a segment of the fistula; removing tissue proximate the fistula; blocking a sidebranch proximate the fistula; and combinations of these. A fistula modifying device can include one or more devices selected from the group consisting of: an over the wire device constructed and arranged to be delivered over a vessel-to-vessel guidewire as described herein; an expanding scaffold configured to increase or otherwise modify fistula geometry such as an expandable balloon; an energy delivery catheter such as a catheter configured to deliver energy to tissue proximate a fistula; an agent delivery catheter such as a catheter configured to deliver an agent such as a pharmaceutical agent or an adhesive such as fibrin glue; and combinations of these.

The method of the present inventive concepts can include the performance of one or more diagnostic procedures that produce diagnostic data, such as the diagnostic procedures described in reference to STEP 10 and STEP 30 hereabove. In some embodiments, a fistula is sized, formed or otherwise based on the produced diagnostic data. In some embodiments, a fistula parameter (e.g. flow rate; cross sectional area; length; and/or diameter) is based on patient blood pressure data, such as blood pressure data that is gathered over a period of time of at least sixty minutes. One or more fistula parameters can be based on a patient data selected from the group consisting of: central blood pressure data; vascular tone data; central sympathetic tone data; cardiac output data; peripheral vascular resistance data; and combinations of these.

In some embodiments, a second clinical procedure is performed in addition to the creation of the fistula, such as a second treatment on the patient performed in STEP 40. In some embodiments, a second fistula is created, such as using the techniques of STEP 20 described hereabove. The second fistula can be created in the same clinical procedure as STEP 20 (in which the first fistula is created), or in a subsequent clinical procedure such as a procedure performed at least twenty-four hours after completion of STEP 20, or at least 1 week, at least 1 month, and/or at least 6 months after completion of STEP 20. A second fistula can be created due to inadequate therapy provided by the first fistula, and/or if the first fistula has insufficient flow (e.g. becomes non-patent). A second fistula can be created due to formation of a vascular (e.g. venous) stenosis proximate the first fistula. In these embodiments, the first fistula can be reversed (e.g. closed), such as through the placement of a covered stent graft in the vein or artery that covers the fistula, or other fistula-occlusive procedure.

A second clinical procedure performed on the patient can comprise a non-fistula creation procedure. The second clinical procedure can comprise a treatment selected from the group consisting of: delivery of a pharmaceutical agent; performance of a Cox-Maze procedure; performance of a cardiac ablation procedure; performance of a valve treatment; performance of a renal denervation procedure; a renal vessel dilation procedure; a renal vessel stenting procedure; and combinations of these. The second clinical procedure can be performed concurrent with the fistula creation procedure; within twenty four hours of the fistula creation procedure; prior to the fistula creation procedure (e.g. at least 1 week or at least 6 months prior); and/or after the fistula creation procedure (e.g. at least 1 week or at least 6 months after). In some embodiments, the second clinical procedure comprises the delivery of a pharmaceutical agent such as an anti-arrhythmia drug and/or an anti-thrombotic (e.g. blood thinning) drug. In some embodiments, the second treatment comprises a cardiac ablation procedure selected from the group consisting of: a surgical ablation procedure;

an interventional ablation procedure; a pulmonary vein isolation procedure; a left atrial posterior wall ablation procedure; a left atrial septum ablation procedure; and combinations of these. The second clinical procedure can comprise a cardiac ablation procedure using a form of energy selected from the group consisting of: radiofrequency energy; laser energy; ultrasound energy; chemical energy; and combinations of these. In some embodiments, the second procedure comprises a valve treatment comprising valvuloplasty of a cardiac valve. In some embodiments, the second clinical procedure can comprise a renal denervation procedure, such as a renal denervation procedure performed prior to, concurrent with and/or after the fistula creation procedure. In these embodiments, the fistula may be created based on a blood pressure reduction that results from the renal denervation procedure, such as a diastolic and/or systolic blood pressure reduction caused by renal denervation.

The method of FIG. 1 can be performed using real-time imaging, such as real-time imaging provided by a fluoroscope and/or an ultrasound imaging device.

In some embodiments, the method of FIG. 1 can be performed to cause a reduction in central sympathetic neural activity. In other embodiments, the fistula is created to reduce a patient parameter selected from the group consisting of: peripheral vascular resistance; left ventricular preload; left ventricular pressure; left atrial volume; left atrial volume; left atrial stretching; and combinations of these. In some embodiments, the fistula is created to treat systemic arterial hypertension, such as drug-resistant hypertension. In some embodiments, the fistula is created to provide a reduction in diastolic and/or systolic blood pressure. In these embodiments, the reduction in systolic blood pressure can be of relatively equivalent magnitude to the reduction in diastolic blood pressure. In some embodiments, the fistula causes an increased compliance in the arterial vascular system. The fistula or a resultant physiologic change due to the fistula can cause a release of one or more of chemo-receptors or vaso-dilating factors. In some embodiments, the fistula is created and/or modified based on a measurement of at least one of vascular tone or vascular compliance.

In some embodiments, the method of FIG. 1 can be performed to lower blood pressure within an organ of the patient, such as an organ selected from the group consisting of: liver; kidney; heart; brain; and combinations of these.

The method of FIG. 1 can be performed to decrease peripheral vascular resistance, such as to decrease infrarenal vascular resistance (e.g. below the kidneys or in a manner to include the great vessels of the aorta and/or the inferior vena cava). Alternatively or additionally, the method can be performed to achieve a physiologic change selected from the group consisting of: increased oxygen delivery by the arterial system; increased blood volume; increased proportion of blood flow to the descending aorta; increased blood flow to the kidneys; increased blood flow outside the kidneys; increased cardiac output; and combinations of these. The method can be constructed and arranged to prevent any significant chronic increase in heart rate. Alternatively or additionally, the method can be constructed and arranged to prevent a decrease in cardiac function. Alternatively or additionally, the method can be constructed and arranged to avoid undesired adverse effects to the kidneys, such as by avoiding the adverse effects that can be encountered in a renal denervation procedure, such as stenosis, lost autonomic control and/or vessel intima damage.

In some embodiments, the method is performed to increase oxygenation and/or flow rates associated with the patient's chemo-receptors, such as to cause a therapeutic change to vascular resistance. In some embodiments, the method is performed to affect or otherwise modify the patient's central sympathetic tone. Modifications to central sympathetic tone can be performed to reduce systolic and/or diastolic blood pressure (e.g. mean systolic and/or mean diastolic blood pressure), and/or to treat other patient diseases and conditions such as diabetes, sleep apnea, or heart failure.

In some embodiments, the method of FIG. 1 is constructed and arranged to cause a reduction in diastolic blood pressure that is equal to or greater than a concurrent reduction in systolic blood pressure, such as are presented in Table 3 described herebelow. In some embodiments, the method is constructed and arranged to reduce the diastolic pressure more than the systolic pressure by an amount of at least 2 mmHg, at least 4 mmHg or approximately 5 mmHg. In some embodiments, the method is constructed and arranged to reduce the diastolic pressure by at least 5 mmHg, such as a reduction of at least 10 mmHg, at least 15 mmHg or approximately 18 mmHg. In some embodiments, the method is constructed and arranged to reduce the systolic pressure by at least 5 mmHg, such as a reduction of at least 10 mmHg or approximately 13 mmHg. In some embodiments, the method is constructed and arranged to cause a reduction in blood pressure to a level at or below 130/90 mmHg.

The method of FIG. 1 and associated clinical testing has been performed by applicant in a study in patients with hypertension and COPD. In the study, the patients with hypertension received a significant and beneficial drop in blood pressure as a result of the fistula creation. Twenty four of the patients studied had systolic pressure greater than 130 mmHg. In each patient, a 4 mm fistula was created to shunt blood from the right iliac artery to the right iliac vein. Cardiac output was measured before and after the procedure, and blood pressure was recorded before the procedure and again at 3, 6, 9 and 12 months. The creation of a fistula in the iliac region increased cardiac outputs by 41% ($p<0.01$), with a mean percentage change of 44%. An unexpected outcome was that patients with high blood pressure soon had a substantial drop in both their systolic and diastolic blood pressures. In previously performed large population studies, a 10 mmHg drop in systolic blood pressure has been associated with a 40% reduction in risk of stroke mortality and a 30% reduction in risk of death due to coronary disease. A year after the procedure, average drop in systolic blood pressure was 13 mmHg lower (SD 17; $p<0.01$) and the average drop in diastolic blood pressure was 18.4 mmHg (SD 12; $p<0.0001$). The only significant adverse effect of the procedure was the development of venous stenosis in the iliac vein above the site of the fistula. This adverse event occurred in four subjects, but was corrected by placing a covered stent in the iliac vein over the fistula. Detailed information on the study is provided immediately herebelow.

Methods & Participating Patients

Patients were selected based on several inclusion and exclusion criteria, including the ability to undergo arteriovenous fistula creation, GOLD Stage II or greater COPD, and participants were without a current exacerbation of COPD and were on stable medication for a minimum of 4 weeks prior to enrollment. The criteria for exclusion included pulmonary arterial hypertension (a mean Pulmonary Arterial Pressure greater than 35 mmHg), obesity (Body Mass Index greater than 31 kg·m-2 male or 32 kg·m-2 female), liver cirrhosis, recent stroke or heart failure (within 6 months), unstable coronary artery disease, and malignant cancer that might adversely affect the subject's safety. A large group of patients (n=67) had an arteriovenous fistula created as part of a multi-center international study of arteriovenous fistula creation in patients with severe COPD. In addition to parameters concerned with exercise capacity and pulmonary function, subjects were also evaluated for office-based blood pressure and hemodynamic measures during cardiac catheterization at baseline and follow-up. Of particular note were twenty four subjects with high blood pressure (subjects who, in spite of anti-hypertensive therapy had systolic blood pressure recordings greater than 130 mmHg at baseline) who were not known to have a secondary cause of hypertension. Blood pressure and hemodynamic changes in those twenty four hypertensive subjects are reported herein. Patients underwent percutaneous arteriovenous fistula creation using an anastomotic clip such as anastomotic clip 160 of FIG. 2 described herebelow. Assessment included physical examination, clinic based blood pressure recordings, and cardiac catheterization to measure cardiac output, oxygen delivery, and both pulmonary and systemic vascular resistances.

Procedure

In each procedure, an anastomotic clip was deployed in the iliac region to create an iliac arteriovenous fistula. Vascular femoral venous and arterial access was obtained using standard interventional techniques. FIGS. 3A and 3B illustrate the 7 Fr anastomotic clip delivery device used, including the anastomotic clip which was implanted. In some embodiments, the anastomotic clip delivery device comprises device 150, and the anastomotic clip comprises device 160, each of FIG. 2 herebelow. In FIG. 3C, an angiogram of the iliac artery A and iliac vein V prior to shunt creation is illustrated. A vessel targeting wire CW, such as wire 120 of FIG. 2, outlines the iliac artery, and a venogram confirms vessel proximity and target crossing location for the creation of the arteriovenous fistula. A 22 gauge crossing needle, such as a needle of deployment device 140 of FIG. 2 herebelow, is placed into the vein over a guidewire and through an 11 Fr introducer device, not shown but such as introducer 110 also of FIG. 2 herebelow. The 22 gauge crossing needle has been advanced through the wall of the iliac vein into the iliac artery, and a guidewire advanced through a lumen of the needle and into the artery. In the procedure, the needle was subsequently removed and the anastomotic clip delivery system tracked across the puncture site. The anastomotic clip was then deployed so that the expanded arms of the anastomotic clip attached to the inner walls of the iliac artery and iliac vein, and the retention arms maintained the anastomotic clip in the proper position (deployed position shown in FIG. 3D). After removal of the delivery system, a 4-mm balloon catheter was inserted into the center of the anastomotic clip and inflated to expand the anastomotic clip to a 4-mm diameter. The balloon was then deflated and removed. An angiogram confirmed the patency of the fistula. Subjects were prescribed aspirin and compression stockings after the procedure.

Baseline measurements consisted of vital signs, physical examination and cardiac catheterization. Follow-up assessments were performed at 3, 6, 9, and 12 months, which consisted of office blood-pressure measurement, physical examination, and surveillance for adverse events. Blood pressures were recorded in an office setting and in accordance with standard Joint National Committee VII guidelines. Subjects also underwent repeat cardiac catheterization 3 to 6 months after the creation of the fistula. Cardiac output was measured in all but five subjects using a thermodilution catheter technique. In five subjects the baseline and follow-up cardiac output were measured using the Fick technique.

Statistical Analysis

All blood pressure analyses were performed post-hoc. Changes in office-based blood pressure were analyzed over 12 months of follow-up and compared with baseline blood pressure by repeated measures analysis of variance with pair-wise comparison of significant values. To assess the hemodynamic effect of arteriovenous fistula creation, hemodynamic measures were compared between baseline and repeat cardiac catheterization (between 3 and 6 months after the creation of the fistula) using paired t-tests. Adverse events were also recorded. A p value of less than 0.05 was regarded as statistically significant. Multiple linear regression analysis was performed to determine whether an association exists between changes in hemodynamic measures and changes in office based blood pressure and age, gender, baseline heart rate, and baseline severity of COPD.

Results—Characteristics of the Patients:

While testing the creation of an iliac arteriovenous fistula using a percutaneously deployed nitinol anastomotic clip in sixty-seven patients with COPD, twenty-four (13 male) subjects were included who had both a systolic blood pressure greater than 130 mmHg and severe COPD (mean post-bronchodilator FEV1=30% predicted). The procedure was successful in all cases. Their demographic details are contained in Table 1. Two thirds of patients (n=16) had a systolic blood pressure greater than 140 mmHg at baseline, while 21% had a systolic blood pressure greater than 160 mmHg. There was no gender or race/ethnic based difference in outcome. Arterial blood pressure at enrollment was 145/86 mmHg (SD 12/13), with a heart rate of 91 beats per minute (SD 16). Patients took, on average, 2 anti-hypertensive medications, with (29%) receiving an angiotensin-converting enzyme inhibitor, (17%) an angiotensin II receptor blocker, (17%) beta-blockers, (25%) calcium-channel blockers, and (8%) direct vasodilators. Almost half (46%) of the hypertensive patients also took diuretics as shown in Table 1 immediately herebelow.

TABLE 1

Baseline demographics of the 24 subjects with severe COPD and hypertension who underwent creation of the arteriovenous fistula.

| | |
|---|---|
| Number of subjects | 24 |
| Age years | 65 (6) |
| Male gender | 54% |
| Body mass index kg · m$^{-2}$ | 25 (5) |
| Cigarette consumption (pack years) | 47 (25) |
| Systolic blood pressure mmHg | 145 (12) |
| Diastolic blood pressure mmHg | 86 (13) |
| Mean arterial blood pressure mmHg | 105 (12) |
| Serum creatinine mg/dl | 0.84 (.26) |
| Diuretic | 46% |
| ACE inhibitor | 29% |
| Angiotensin receptor blocker | 17% |
| Beta-blocker | 17% |
| Vasodilator (nitrate) | 8% |
| Calcium channel blocker | 25% |
| Post-bronchodilator FVC (% predicted) | 68 (22) |
| Post-bronchodilator FEV$_1$ (% predicted) | 30 (11) |
| PaO$_2$ mmHg on Room air | 63 (9) |
| PaCO$_2$ mmHg on Room air | 42 (6) |

Data are presented as mean (standard deviation).

Results—Blood Pressure Lowering Effect:

The average blood pressure measurements were: 145/86 mmHg, 139/76 mmHg, 130/71 mmHg, 132/74 mmHg, and 132/67 mmHg at baseline, 3 months, 6 months, 9 months, and 12 months respectively, as shown in FIGS. 3E and 3F. By the end of the study period (12 months) the systolic blood pressure was reduced from 145 (SD 12) mmHg to 132 (SD 18) mmHg (p<0.01) and the diastolic blood pressure was reduced from 86 (SD 13) mmHg to 67 (SD 13) mmHg (p<0.0001). Multiple comparison testing revealed significant differences in systolic blood pressure between baseline and 3 months, baseline and 6 months, baseline and 9 months, and baseline and 12 months and a significant difference was also seen between 3 months and 12 months, as shown in FIG. 3E and FIG. 4. Multiple comparison testing revealed significant differences in diastolic blood pressure between baseline and 6 months, baseline and 9 months, and baseline and 12 months, as is shown in FIG. 3F and FIG. 4. Multivariable analysis showed a significant association between baseline diastolic blood pressure and changes in diastolic pressure at 12 months (p<0.02) but failed to show a clear association between blood-pressure reduction and any of the following: age, gender, baseline heart rate, baseline severity of COPD (PaO2 and FEV1). At baseline, patients were taking an average of two anti-hypertensive medications, which did not change during follow-up.

Results—Hemodynamic Changes Assessed During Cardiac Catheterization:

Cardiac catheterization revealed increases in cardiac output (from 6 (SD 2) liters/min at baseline to 8.4 (SD 3) liters/min, p<0.001) and oxygen delivery (from 1091(SD 432) ml/min to 1441(SD 518) ml/min, p<0.001), accompanied by reductions in mean arterial pressure (106 (SD 12) mmHg to 97 (SD 12) mmHg, p<0.001), systemic vascular resistance (1457 (SD 483) dynes to 930 (SD 335) dynes, p<0.001), and pulmonary vascular resistance (190 (SD 117) dynes to 140 (SD 77) dynes, p<0.01). Although no change was detected in the right atrial pressures and heart rates, there were small but significant increases in both the pulmonary arterial pressure (25 (SD 5) mmHg at baseline to 29 (SD 6) mmHg at follow-up, p<0.01), and the pulmonary capillary wedge pressure (12.2 (SD 5) mmHg at baseline to 15.5 (SD 7) mmHg at follow-up, p=0.01). Multivariable regression revealed an association between changes in cardiac output and changes in pulmonary vascular resistance (p<0.05) and between changes in cardiac output and changes in systemic vascular resistance (p<0.05). Changes in pulmonary capillary wedge pressure (PCWP) were associated with changes in systemic vascular resistance (p<0.05) but were not associated with changes in pulmonary vascular resistance (PVR).

The median procedure time (from skin to skin) was 53 minutes (range 20 minutes to 2 hours and 15 minutes). Among the 24 patients who underwent arteriovenous fistula creation, the procedure was completed without complication in 20 of the patients. Within 7 days of the procedure, two patients developed pseudoaneurysm at the femoral access site, which was successfully treated with manual compression; one patient developed mild chest pressure and chest pain, which resolved; and one patient developed a clot around the fistula which resolved after anti-coagulant therapy. Late adverse events included four patients who developed deep venous thrombosis (resolved with anti-coagulation) and another patient in whom the shunt was closed in a separate clinical procedure (at 11 months), because of a lack of clinical improvement. Four subjects developed a venous stenosis of the iliac vein cephalad to the device. Two of these cases were initially treated with dilatation, however the stenosis recurred, and they were then successfully treated with stent placement. The other pair was successfully treated with stent placement without recurrence. In one case, the stent was undersized, resulting in dislodgement and migration into the right ventricle. The stent was retrieved and repositioned in the left iliac vein with no sequelae, and the venous stenosis was successfully treated with an appropriately sized self-expanding stent. There was no death during the 12-month follow-up period. In patients whose baseline creatinine level was higher than 1.0 mg/dl (n=4, average creatinine was 1.29 mg/dl, range 1.05 to 1.51 mg/dl), there was a significant increase in glomerular filtration rate, eGFR (MDRD). Their eGFR at 12 months was increased to 67 (SD 18) ml/min from 54 (SD 18) ml/min at baseline, (p=0.02).

Discussion:

The study provides significant data demonstrating the efficacy of the methods, systems and devices of the present inventive concepts to treat hypertension. Patients suffering from arterial hypertension that received a peripheral arteriovenous fistula had a significant reduction in their blood pressure. A year after the procedure, their systolic blood pressures are an average of 13 mmHg lower, and their diastolic pressures are an average of 18 mmHg lower. In fact, the higher the diastolic pressure before the procedure, the greater is the drop in diastolic pressure. The number of patients with hypertension (a systolic blood pressure greater than 140 mmHg) is halved (16 to 8).

The methods, systems and device of the present inventive concepts provide a painless percutaneous procedure producing rapid reductions in blood pressure. Deployment of the device employs iliofemoral vascular access with a catheter guidance system, and (through a series of crossing needles and dilators) creation of a 4 mm fistula between the iliac artery and iliac vein. The fistulas remained patent (100% patency rate at 1 year) and is remarkably well tolerated, even in these elderly patients with advanced lung disease.

Blood pressure lowering effect is not the only hemodynamic effect of this procedure. Our hemodynamic data obtained via cardiac catheterization correlate to increased cardiac output and oxygen delivery, and the study results demonstrated significant reductions in pulmonary vascular resistance and systemic vascular resistance. The drop in pulmonary vascular resistance appears to be associated with changes in cardiac output, rather than increases in pulmonary capillary wedge pressure or increases in mixed venous oxygen content (see Table 2 herebelow). This drop in pulmonary vascular resistance is supported by applicant's work on pulmonary hypertensive disease in rats, which showed that the creation of a modest arteriovenous shunt attenuates rather than accelerates the development of pulmonary vascular disease.

TABLE 2

Hemodynamic values at baseline and on repeat cardiac catheterization post insertion of the arteriovenous anastomotic clip (n = 23).

|  | Baseline | Repeat* | p value |
| --- | --- | --- | --- |
| Heart rate (bpm) | 91 (16) | 92 (16) | 0.85 |
| Mean arterial pressure mmHg | 106 (12) | 97 (12) | 0.001 |
| Right atrial pressure mmHg | 8 (4) | 9.5 (4) | 0.17 |
| Cardiac output (liters/min) | 6 (2) | 8.4 (3) | <0.001 |
| Oxygen delivery (ml. min.$^{-1}$) | 1091 (432) | 1441 (518) | <0.001 |
| Systemic vascular resistance dynes | 1457 (483) | 930 (335) | <0.001 |
| Mean pulmonary arterial pressure mmHg | 25 (5) | 29 (6) | <0.01 |
| Mixed venous oxygen saturation % | 73 (6) | 79 (5) | <0.001 |
| Pulmonary capillary wedge pressure mmHg | 12.2 (5) | 15.5 (7) | 0.01 |
| Pulmonary vascular resistance dynes | 190 (117) | 140 (77) | <0.01 |

*Repeat cardiac catheterization was performed between 3 and 6 months after creation of an arteriovenous fistula.

Table 3 herebelow represents ambulatory blood pressure data for eight patients who received the fistula creation procedure of the present inventive concepts. The data includes daytime and nighttime blood pressures for each patient at baseline and 1 month, 3 months and 6 months after the fistula creation procedure. Patient 1 and Patient 3 daytime blood pressure significantly decreased at nighttime over six months as compared with baseline blood pressure. Patient 2 is a diabetic on multiple medications and saw a significant decrease in daytime blood pressure by six months. Patient 4 received Tegretol (carbamaepine) and Lipitor (atorvastatin) between baseline and three months. Patient 5 is resistant to all hypertension medications. Patient 6 nighttime blood pressure significantly decreased at three months such that the patient's blood pressure decreased from daytime to nighttime. Patient 7 diastolic blood pressure significantly dropped in the daytime and nighttime by 1 month. Patient 8 systolic blood pressure entered normal range in the daytime and nighttime at 1 month.

TABLE 3

Ambulatory Blood Pressure (BP) Daytime/Nighttime Changes for 8 Patients

| Patient | Baseline Day | Baseline Night | 1 Mo Day | 1 Mo Night | 3 Mo Day | 3 Mo Night | 6 Mo Day | 6 Mo Night |
|---|---|---|---|---|---|---|---|---|
| 1 | 162/98 | 150/90 | 159/78 | 132/60 | 158/80 | 140/69 | 160/75 | 135/60 |
| 2 | 159/72 | 126/64 | 158/67 | 134/59 | 135/55 | 126/53 | 133/57 | 124/53 |
| 3 | 152/86 | 138/73 | 151/76 | 133/64 | 144/77 | 127/63 | 143/71 | 127/61 |
| 4 | 163/76 | 147/72 | 148/65 | 139/62 | 158/71 | 154/68 | — | — |
| 5 | 189/113 | 181/108 | 197/103 | 166/88 | 192/110 | 182/99 | — | — |
| 6 | 135/69 | 131/62 | 129/59 | 125/61 | 138/69 | 119/60 | — | — |
| 7 | 143/86 | 149/89 | 145/71 | 146/74 | — | — | — | — |
| 8 | 140/74 | 133/68 | 127/60 | 126/61 | — | — | — | — |

Table 4 herebelow represents average serum creatinine data for three patients who received the fistula creation procedure of the present inventive concepts. The data includes serum creatinine levels for three patients having Stage II Hypertension and elevated serum creatinine levels for four patients at baseline at baseline and three months, six months, nine months, and twelve months after the fistula creation procedure. The data indicates a sustained decrease in serum creatinine levels representative of increased kidney perfusion, thus improved renal function. The analysis showed no correlation between change in serum creatinine and weight over the course of the twelve months follow up.

TABLE 4

Average serum creatinine levels for 3 Patients representative of increased kidney perfusion and improved renal function

| | Baseline | 3 Mo | 6 Mo | 9 Mo | 12 Mo |
|---|---|---|---|---|---|
| Serum Creatinine Levels (mg/dL) Stage II Hypertension | 1.10 | 0.96 | 0.95 | 0.85 | 0.90 |
| Serum Creatinine Levels (mg/dL) Elevated Levels at Baseline | 1.29 | 1.30 | 1.10 | 1.00 | 1.04 |

Table 5 herebelow represents the results from an evaluation of cardiac function for patients who received the fistula creation procedure of the present inventive concepts. Echocardiogram results demonstrated no change, and in some cases, an improvement to cardiac function for those patients receiving the fistula creation procedure. Control data indicated a decline in cardiac function for some patients.

TABLE 5

Change in Cardiac Function: Data represented by # of patients/total # of patients

| | ROX Device | | Control | |
|---|---|---|---|---|
| | 6 Month | 12 Month | 6 Month | 12 Month |
| No Change | 15/19 | 11/15 | 13/20 | 11/16 |
| Improvement | 4/19 | 3/15 | 3/20 | 1/16 |
| Decline | 0/19 | 1/15 | 4/20 | 4/16 |

Figure 2:
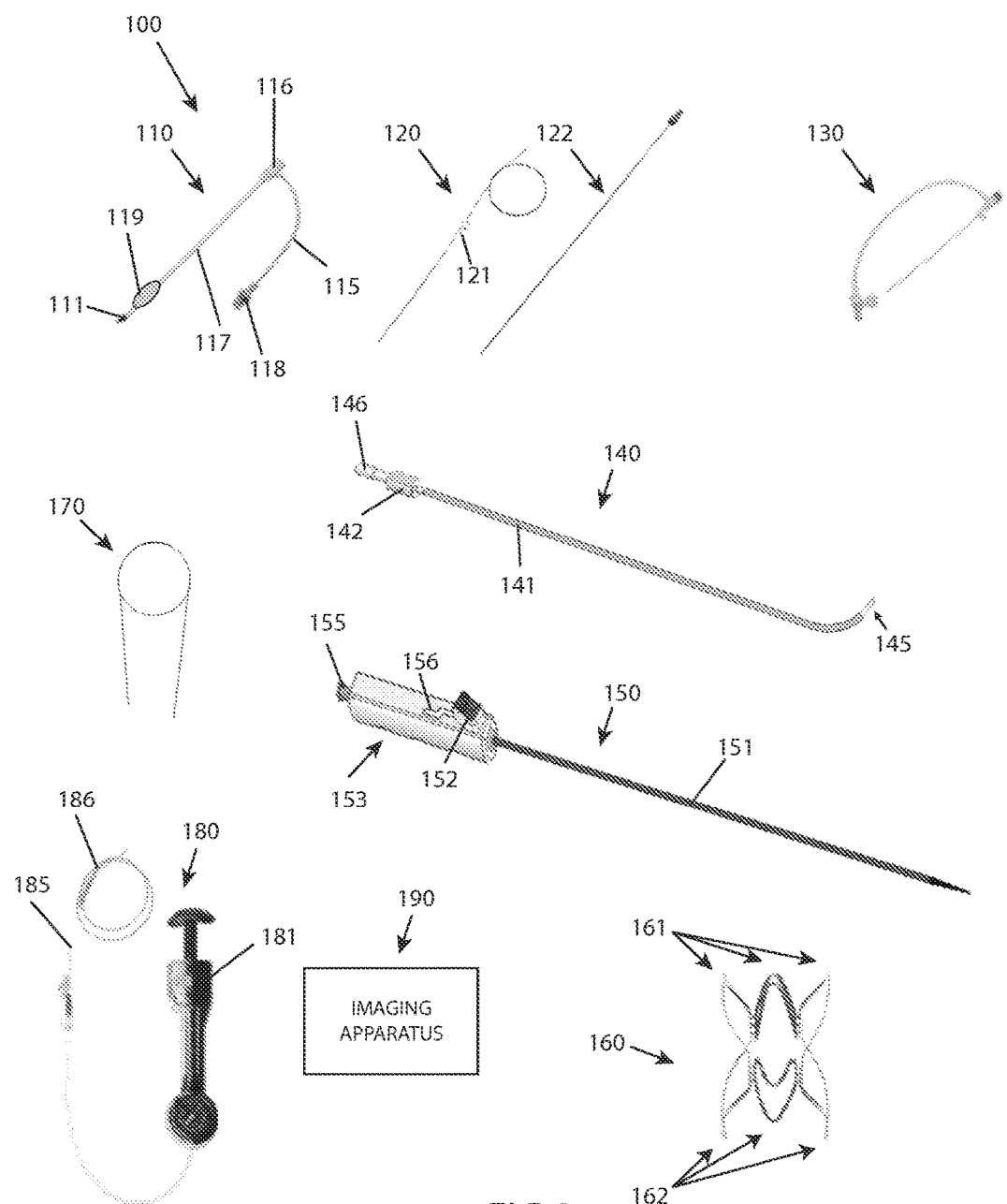
FIG. 2 is a schematic view of a system for creating a flow pathway in a patient, consistent with the present inventive concepts.
Figure 3A:
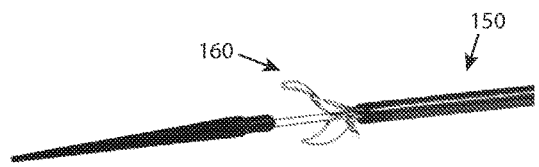
FIGS. 3A through 3D are a set of steps for implanting an anastomotic clip, consistent with the present inventive concepts.
Figure 3B:
Figure 3C:
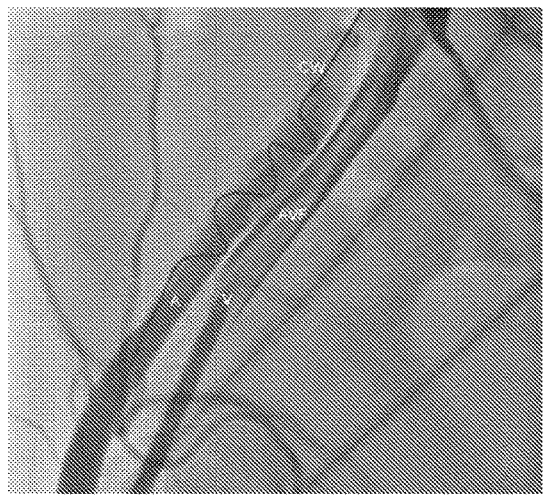
Figure 3D:
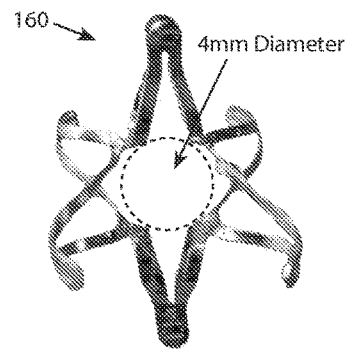

Referring now to FIG. 2, a system for creating a fistula between a first vascular location in a patient's arterial system of a patient (e.g. an artery), and a second vascular location in the patient's venous system (e.g. a vein), is illustrated. System 100 can be constructed and arranged to create a fistula to treat a cardiac arrhythmia of a patient and/or to improve a function of a cardiac structure. Alternatively or additionally, system 100 can be constructed and arranged to treat a patient disease or disorder selected from the group consisting of: chronic obstructive pulmonary disease; congestive heart failure; lung fibrosis; adult respiratory distress syndrome; lymphangioleiomytosis; pulmonary hypertension; sleep apnea such as sleep apnea due to hypoxemia or hypertension; and combinations of these. System 100 comprises a vascular introducer, first introducer 110, configured to be placed into the patient to provide access to a starting vessel. System 100 comprises another vascular introducer, second introducer 130, configured to provide access to a target vessel. In some embodiments, the starting vessel is a vein, and the target vessel is an artery. In other embodiments, the starting vessel is an artery and the target vessel is a vein. System 100 can include target wire 120 which comprises helical section 121 and is configured to be placed through the second introducer 130 and into the target vessel. Target wire 120 can be placed through an elongate tube, catheter 122. System 100 can comprise needle deployment device 140 which is configured to deploy crossing needle 145 (shown in an advanced position in FIG. 2), from the starting vessel and into the target vessel. System 100 can include a vessel-to-vessel guidewire 170, which can be placed from the starting vessel to the target vessel via needle deployment device 140. System 100 can also include clip deployment catheter 150, which is configured to deploy anastomotic clip 160. System 100 can include a fistula modifying device, such as dilation device 180 including balloon catheter 185 and standard angioplasty balloon indeflator 181. System 100 can further comprise imaging apparatus 190, typically a fluoroscope and/or ultrasound imaging device used to image one or more device or components of system 100, as well as the patient's anatomy, during the creation of an arteriovenous fistula.

First introducer 110 is configured to be placed into the patient to provide access to a starting vessel (e.g. a vein of a patient). In some embodiments, introducer 110 comprises an 11 French vascular introducer. First introducer 110 can comprise beveled tip 111 with an angle ranging from 20° to 50°, such as at an angle of approximately 30°. Additionally, system 100 can include a kit comprising an additional introducer having a second angle providing the clinician or other user (hereinafter "clinician) with more options as may be appropriate for a particular patient's anatomical geometry. In some embodiments, beveled tip 111 comprises a marker, for example, a radiopaque or other visualizable marker, such that the luminal wall of the starting vessel can be imaged (e.g. when tip 111 is pressed against the vessel wall). The proximal portion of introducer 110 can comprise a contour or marker, such as to be correlated with or otherwise indicate the alignment of the bevel of tip 111.

Introducer 110 comprises shaft 117 which includes at least one thru lumen. Introducer 110 also comprises port 116, typically a hemostasis valve, which is fluidly connected to the lumen of shaft 117. A second port 118, typically a luer connector, is connected to tubing 115 which in turn is connected to port 116. Introducer 110 can further comprise a dilator, not shown but typically an 11 to 13 Fr dilator used to introduce and/or pre-dilate tissue receiving introducer 110. Introducer 110 can further comprise a radially expandable element, such as expandable element 119, such as a balloon or expandable cage located on its distal portion. In some embodiments, expandable element 119 can be configured to prevent advancement of introducer 110 into the target vessel. In yet another embodiment, expandable element 119 can be configured to stabilize the starting vessel during insertion of introducer 110 or another device or component of system 100.

System 100 can comprise second introducer 130 which is configured to provide access to a target vessel, such as an artery of the patient when the starting vessel is a vein. In some embodiments, second introducer 130 comprises a 4 French vascular introducer. System 100 comprises target wire 120 configured to be placed through second introducer 130 and into the target vessel. Target wire 120 can comprise helical section 121 configured to be deployed at the site where the fistula is to be created. Helical section 121 can be configured to provide structure and support to the site during a procedure. Additionally, target wire 120 can serve as a visual reference during insertion of vessel-to-vessel guidewire 170, as described herebelow.

System 100 can comprise needle deployment device 140. Needle deployment device 140 comprises shaft 141 which slidingly receives advanceable crossing needle 145, shown in an advanced state. Shaft 141 comprises shaft hub 142 mounted to its proximal end. Shaft 141 can comprise a curved distal portion as shown. Crossing needle 145 comprises needle hub 146 mounted to its distal end. Movement of needle hub 146 relative to shaft hub 142 causes crossing needle 145 to advance and retract within shaft 141. Needle hub 146 is fully advanced toward shaft hub 142 in the configuration of FIG. 2, such that the tip and distal portion of crossing needle 145 is fully advanced out of the distal end of shaft 141.

Crossing needle 145 can comprise a 20 to 24 gauge needle, such as a 22 gauge needle. In some embodiments, the crossing needle 145 comprises a curved distal portion (as shown). The curved distal portions of shaft 141 and/or needle 145 can be aimed at the center of the target vessel prior to insertion into the target vessel. The radius of curvature can be reduced if the clinician has difficulty in aiming the needle tip at the center of the target vessel prior to insertion. Conversely, the radius of curvature can be increased to sufficiently aim the needle tip at the center of the target vessel. Additionally, the crossing needle 145 can comprise a marker, not shown but indicating the direction of curvature. Examples of markers include, but are not limited to: a flat surface, a textured surface; a visualizable marker such as a radiopaque marker, a magnetic marker, an ultrasonic marker or a visible marker; and combinations of these. In some embodiments, crossing needle 145 can comprise a shaped memory alloy, for example, nickel titanium alloy. In some embodiments, shaft hub 142 and/or needle hub 146 comprise a marker or other visible demarcation (e.g. a flat portion) which correlates to the direction of curvature of shaft 141 and/or crossing needle 145, respectively.

System 100 can comprise a guidewire to be placed from the starting vessel to the target vessel, vessel-to-vessel guidewire 170. Guidewire 170 is configured to be placed via needle deployment device 140. In some embodiments, vessel-to-vessel guidewire 170 comprises a wire with an outer diameter of approximately 0.018". Vessel-to-vessel guidewire 170 can comprise a marker, not shown but configured to indicate the fistula location. In some embodiments, vessel-to-vessel guidewire 170 comprises a distal portion and a mid portion. Guidewire 170 mid portion can comprise a different construction than the distal portion. For example, the mid portion of guidewire 170 can be stiffer than the distal portion.

System 100 can comprise clip deployment catheter 150 configured to house and deploy anastomotic clip 160. Clip 160 comprises a plurality of distal arms 161 and a plurality of proximal arms 162, which can be deployed simultaneously or independently. Clip 160 comprises at least two distal arms 161 and at least two proximal arms 162 configured to deploy and engage the starting vessel and the target vessel. In some embodiments, clip 160 comprises four deployable distal arms 161 and four deployable proximal arms 162. Clip 160 can comprise a shaped memory alloy, such as nickel titanium alloy. In some embodiments, clip 160 is constructed and arranged as described in applicant's U.S. Pat. No. 7,828,814, entitled "Device and Method for Establishing an Artificial Arterio-Venous Fistula", filed Apr. 4, 2007, the contents of which are incorporated herein by reference in its entirety.

In some embodiments, clip 160 is biodegradable or includes one or more biodegradable portions (e.g. one or more portions of clip are absorbed or otherwise degrade over time). In some embodiments, clip 160 comprises a biodegradable anastomotic device such as is described in applicant's co-pending U.S. Non-Provisional application Ser. No. 12/752,397, entitled "Device and Method for Establishing an Artificial Arteriovenous Fistula", filed Apr. 1, 2010, the contents of which are incorporated herein by reference in its entirety.

Clip deployment catheter 150 comprises shaft 151. Mounted to the proximal end of shaft 151 is handle 153. On the proximal end of handle 153 is port 155, which is operably attached to shaft 151 such that a guidewire can travel from the distal end of shaft 151 to port 155, such as guidewire 170 after it has been previously placed between a starting vessel and a target vessel as has been described hereabove. Shaft 151 comprises one or more tubular portions, such as an inner tubular segment that houses clip 160, and an outer tubular segment that covers clip 160 but can be retracted to deploy clip 160, such as is described in applicant's co-pending U.S. Non-Provisional application Ser. No. 11/152,621, entitled "Devices for Arterio-Venous Fistula Creation", filed Jun. 13, 2005, the contents of which is incorporated herein by reference in its entirety.

Handle 153 further includes control 152 (e.g. a button, slide or lever), where control 152 is operably configured to allow an operator to deploy distal arms 161 and/or proximal arms 162 of clip 160, such as via retraction of an outer tube or sheath portion of shaft 151 that is covering one or more portions of clip 160. In some embodiments, a click or other tactile feedback is provided during retraction of a sheath portion of shaft 151. Control 152 can be moved via a stepped or otherwise segmented slot 156. Distal arms 161 can be deployed via moving control 152 from a "first ready to deploy" position to a "first deployed" position which can be achieved by moving control 152 relatively parallel to the longitudinal axis of handle 153. The at least two proximal arms 162 can be queued to be deployed via moving control 152 from the first deployed position to a "second ready to deploy" position. The second ready to deploy position can be achieved by moving control 152 in a direction perpendicular to the longitudinal axis of the handle. Subsequently, proximal arms 162 can deployed via moving control 152 from the second ready to be deployed position to a "second deployed" position via a motion parallel to the longitudinal axis of the handle. In this embodiment, control 152 can include a safety position comprising a ready to deploy position which can be transitioned by moving control 152 in a direction that is perpendicular to the axis of handle 153. This control advancement arrangement can prevent inadvertent deployment of distal arms 161 and/or proximal arms 162.

In some embodiments, prior to deployment of one or more arms of clip 160, introducer 110 can be advanced such that end 111 applies a force to the wall of the starting vessel. Sufficient force can be applied by introducer 110 to enable an operator to "seat" the starting vessel against the target vessel to assist in properly deployment of clip 160.

In some embodiments, catheter 150 can be configured to recapture distal arms 161 and/or proximal arms 162. For example, clip deployment catheter 150 can deploy at least one distal arm 161 and subsequently recapture the at least one distal arm 161.

Clip deployment catheter 150 and/or clip 160 can further comprise at least one marker, not shown but typically a radiopaque and/or ultrasonic marker configured to assist in the rotational positioning of clip 160 at the fistula location. For example, the marker can be oriented toward the target vessel prior to deployment of clip 160. In some embodiments, a marker is included on the distal portion of clip deployment catheter 150. In some embodiments, handle 153 comprises one or more markers that are circumferentially aligned with clip 160 prior to its deployment. In some embodiments, clip deployment catheter 150 and/or clip 160 comprise at least one marker configured to longitudinally position clip 160 at the fistula location. In these embodiments, the marker can indicate the distal and/or proximal end of clip 160.

Clip deployment catheter 150 can further comprise a projection and/or recess, neither shown but configured to mechanically engage clip 160. The project and/or pin can be used to stabilize clip 160 with shaft 151, such as when an outer tubular portion of shaft 151 is advanced or retracted.

System 100 can comprise dilation device 180 configured to dilate clip 160 and/or the fistula. Dilation device 180 can include balloon catheter 185, such as a standard angioplasty balloon catheter comprising balloon 186. Attached to the proximal end of catheter 185 is indeflator 181, typically a standard balloon indeflator device. Alternatively, balloon 186 can comprise a non-balloon expandable such as an expandable cage or radially deployable arms configured to dilate the fistula. Catheter 185 is configured to track over a vessel-to-vessel guidewire, such as guidewire 170 placed between a vein and an artery, such that balloon 186 is positioned within the fistula (e.g. within clip 160). Typically, dilation device 180 can expand to a diameter of less than five millimeters, and more typically to a diameter of approximately four millimeters. In some embodiments, a second dilation device 180 is included, such as a device configured to expand to a different diameter than the first dilation device.

System 100 can include patient imaging apparatus 190. Non-limiting examples of an imaging apparatus include: x-ray; fluoroscope; ultrasound imager; MRI; and combinations of these. The imaging apparatus can allow the clinician to track the movement of all components comprising system 100 as well as view the position of the starting and target vessel relative to each other, as described in detail herein.

System 100 can include an algorithm (e.g. a software based algorithm) used to create the fistula such as an algorithm using a patient parameter (e.g. blood pressure) to determine a fistula parameter such as fistula cross sectional area.

Figure 5:
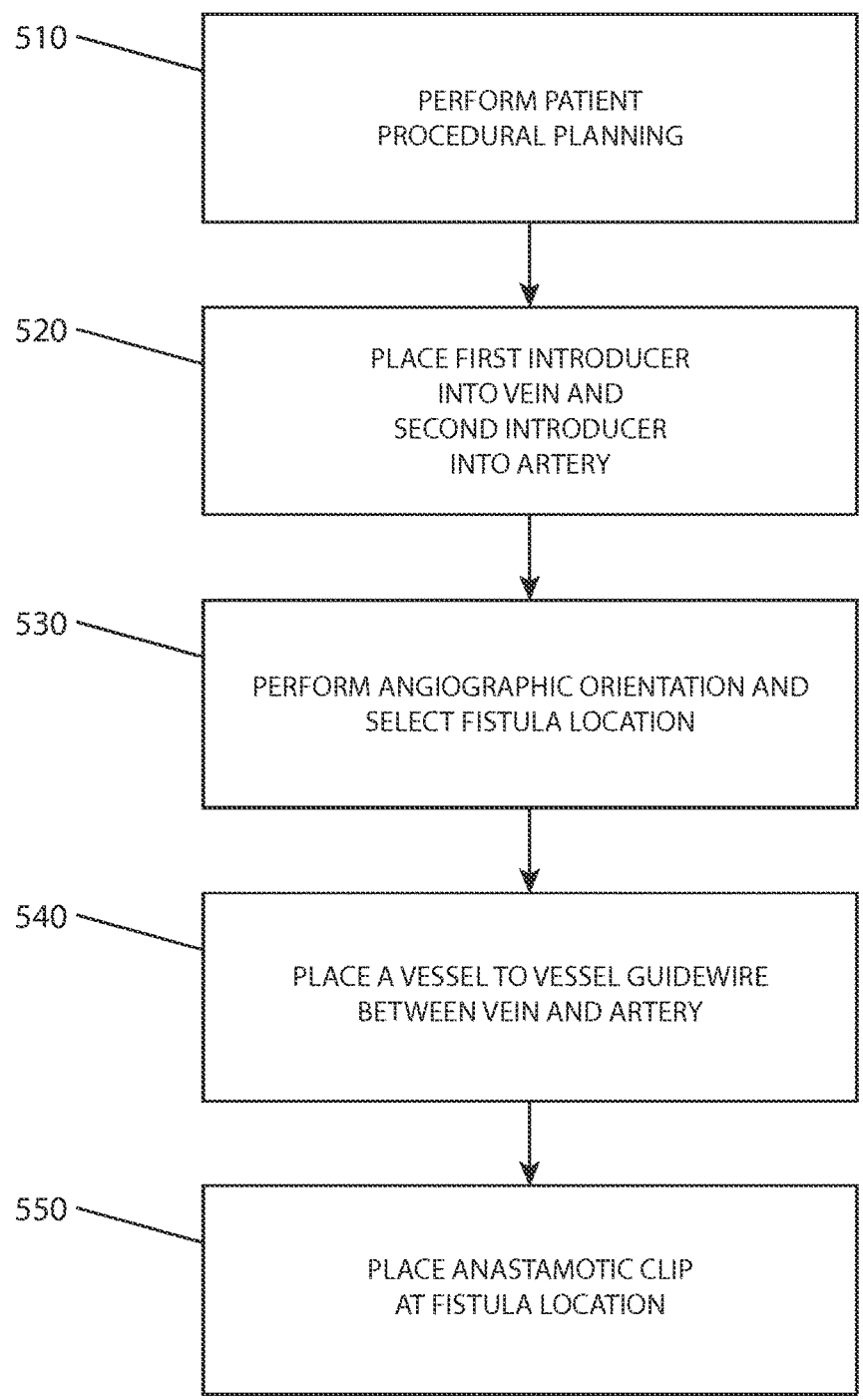
FIG. 5 is a flow chart of a method for treating a patient with a flow pathway, consistent with the present inventive concepts.

Referring now to FIG. 5, a flow chart of a method of creating a fistula between a starting vessel and a target vessel at a fistula location, consistent with the present inventive concepts is illustrated. In STEP 510, a procedural planning assessment of a patient is performed. STEP 520 comprises placing a first introducer into a starting vessel, e.g. a vein, and placing a second introducer into a target vessel, e.g. an artery. In STEP 530, an angiographic orientation is performed and a fistula location is selected. STEP 540 comprises placing a vessel-to-vessel guidewire between the vein and the artery. STEP 550 comprises placing an anastomotic clip at the fistula location. In some embodiments, system 100 and/or one or more components of system 100 of FIG. 2 are used to perform the method of FIG. 5.

The starting vessel can comprise a vein, and can be selected from the group consisting of: inferior vena cava (IVC); saphenous; femoral; iliac; popliteal; brachial; basilic; cephalic; medial forearm; medial cubital; axillary; and jugular. The target vessel can comprise an artery, and can be selected from the group consisting of: aorta; axillary; brachial; ulnar; radial; profundal; femoral; iliac; popliteal and carotid. In a preferred embodiment, the starting vessel and target vessel comprise an external iliac. In an alternate embodiment, the starting vessel can comprise an artery and the target vessel can comprise a vein.

STEP 510, the first step in the illustrated method of the present inventive concepts comprises procedural planning. This step comprises properly orienting the vein and the artery, meaning a clinician becomes familiar with the anatomical orientation of the vein and artery relative to each other. Understanding the orientation of the vessels with respect to one another can be achieved through analysis of one or more images provided by an imaging apparatus (e.g. a fluoroscope) such as imaging apparatus 190 of FIG. 2. In some embodiments, at least one of the vein or artery has a diameter of at least five millimeters proximate the fistula location. In another embodiment, both the vein and artery have a diameter of at least five millimeters proximate the fistula location.

In STEP 520, the method comprises placing a first introducer into the vein. Preferably, the first introducer comprises an 11 French introducer having a beveled tip, such as introducer 110 of FIG. 2 described hereabove. In some instances, the beveled tip of the first introducer can be rotated during insertion into the vein. Rotation of the introducer can be helpful during insertion into the starting vessel due to the tendency of the beveled tip to lift and pull back. Additionally or alternatively, the introducer can be vibrated while it is advanced into the vein. STEP 520 can further comprise pre-dilating the vein with a dilator, preferably a 13 French dilator, prior to placing the introducer into the vein. Additionally, a second introducer can be placed into the artery. Preferably, the second introducer comprises a 4 French introducer, such as introducer 130 described in FIG. 2 hereabove. The method further comprises placing a target wire into the second introducer and then into the artery such that the distal end of the target wire is positioned five to ten centimeters past the fistula location, and configured to serve as a visual reference to a clinician. The target wire, typically including a helical section, is advanced. The advancement can be combined with retracting the introducer such that the helical section of the wire is deployed at the targeted anastomotic site.

In STEP 530, the method comprises performing angiographic orientation and selecting a fistula location. Choosing the fistula location can be based upon a lack of thrombus or other soft tissue occlusive matter at the vascular location, as well as lack of plaque or calcified matter. Preferably, the fistula location is chosen at a location where the vein is less than or equal to three millimeters apart from the artery. Techniques can be used to image the vein and artery in side-by-side configurations as well as overlapping (i.e. on top of each other in the image) orientations. Rotation of the imaging device 90° can modify the provided image from a side-by-side image to an overlapping image, and back again. In some embodiments, after a fistula location has been selected, a clinician can orient the fluoroscope such that the vein and artery are shown overlapping, such as with the vein on top of the artery. In some embodiments, the clinician can position a fluoroscope or other imaging device at an angle to the patient approximating 35° RAO.

In STEP 540, the method comprises placing a vessel-to-vessel guidewire into the vein, such as while the vein and artery are imaged in an overlapping orientation, as described in STEP 530 hereabove. A next step comprises placing a needle delivery device over the vessel-to-vessel guidewire and into the vein. The needle delivery device can comprise a marker, as described in FIG. 2 hereabove, such that a clinician can orient the marker toward the artery. The guidewire can be retracted and subsequently, the needle of the needle delivery device can be advanced toward the target wire and toward the artery. In some embodiments, the vessel-to-vessel guidewire can be placed through a dilator.

Prior to inserting the crossing needle into the artery, a clinician can aim the needle tip at the center of the artery to ensure desired engagement of the artery with the needle, such as by rotating the proximal end of the needle or a device containing the needle. In some embodiments, the needle or needle delivery device includes a proximal hub with a demarcation (e.g. a flat portion or a marker) positioned to indicate the orientation of a curved distal portion of the needle, such as is described in reference to deployment device 140 of FIG. 2 hereabove. In this operation, a clinician can torque or otherwise rotate the needle such that the direction of the needle curvature comes into view on the imaging apparatus (e.g. fluoroscope). Confirming the direction of needle curvature ensures that the needle is to be advanced in the desired direction, such as into the center of the artery. In some embodiments, a target wire is placed in the target vessel, such as vessel-to-vessel guidewire 170 of FIG. 2 described hereabove. Preferably, the needle comprises a curved tip, and the radius of curvature can be reduced if a clinician has difficulty in aiming the needle at the center of the target vessel prior to insertion. Conversely, the radius of curvature can be increased to sufficiently aim the needle tip at the center of the target vessel. In some embodiments, the needle delivery catheter is oriented as described in reference to FIG. 6 herebelow.

Additionally, a clinician can confirm that the distal portion of the vessel-to-vessel guidewire is located within the lumen of the artery. Also, the clinician can confirm the vessel-to-vessel guidewire is parallel with the target wire previously placed in the artery. A clinician can confirm that the needle is positioned within the target vessel by using a dye injection through the needle. Alternatively or additionally, a clinician can confirm that the needle is properly positioned in a target vessel by measuring the pressure in a distal portion of the needle, such as to confirm presence in an artery by confirming arterial pressure is recorded.

In some embodiments, the needle delivery device is placed into the artery and the guidewire is advanced from the artery into the vein via the crossing needle. In these embodiments, the anastomotic clip delivery catheter can also be advanced from artery to vein.

In STEP 550, the method comprises placing an anastomotic clip at a fistula location. Prior to performing STEP 550, placing an anastomotic clip at a fistula location, a user can retract the crossing needle while maintaining the position of the target wire. Next, the target wire can be removed from the second introducer. The target wire can also be removed after STEP 550.

In STEP 550, a user can position the vein and artery such that the vein and artery are slightly apart from each other on the image (e.g. not overlapping). In one embodiment, this can be achieved by rotating a fluoroscopy unit 45° to 90° after an overlapping image is obtained (e.g. an image obtained during a dual contrast injection of both the artery and vein).

Next, the tip of the clip deployment catheter (with a pre-loaded anastomotic clip) can be placed at the fistula site. In this step, a clinician can apply forward pressure and rotate the clip deployment catheter. The clip can comprise at least two distal arms and at least two proximal arms that can be deployed simultaneously or independently via a control located on the handle of the catheter.

STEP 550 further comprises deploying the anastomotic clip in the fistula, such as is described in detail in reference to clip deployment catheter 150 of FIG. 2 hereabove. The clip distal arms are deployed by moving a control on the clip deployment catheter from a ready to deploy position to a first deployed position, which can be achieved by moving the control relatively parallel to the longitudinal axis of the handle. Prior to deploying the proximal arms of the clip, a clinician can retract the first introducer to the fistula location and seat the vein against the artery. The clip deployment catheter can comprise a marker located on its distal end. Using this marker, a clinician can pull the clip deployment catheter back such that the marker is aligned with the distal end of the first introducer.

In a next operation of STEP 550, the proximal arms can be queued to be deployed via moving the control from a first deployed position to a second ready to deploy position. The ready to deploy position can be achieved by moving the control in a direction perpendicular to the longitudinal axis of the handle. Subsequently, the proximal arms can be deployed via moving the control from the second ready to be deployed position to the second deployed position via a motion parallel to the longitudinal axis of the handle. In this embodiment, the control includes a safety position comprising a ready to deploy position which can be transitioned by moving the control in a direction that is perpendicular to the axis of the handle. This control arrangement can prevent inadvertent deployment of the distal and/or proximal arms. After deployment of the proximal arms, a clinician can retract the first introducer from the anastomosis site, such as a retraction of approximately two to three centimeters, followed by retracting the clip deployment catheter.

The method can further comprise dilating the fistula via a balloon or other expandable member. For example, a clinician can track a balloon catheter over the target wire and inflate the balloon. In a typical embodiment, the balloon catheter comprises a diameter of four to five millimeters and can be inflated via a four millimeter by one and one half centimeter non-conforming balloon and indeflator device. The balloon then can be deflated and retracted out of the implant.

The method can further comprise verifying clip patency. This can be achieved via a contrast/saline solution injected into the second introducer. A clinician can then remove all devices once it is confirmed that the clip is positioned as desired.

The method can further comprise placing a second anastomotic clip, such as a second anastomotic clip 160 of FIG. 2 described hereabove. Alternatively or additionally, the method can further comprise creating a second fistula between, such as a second fistula created during the same clinical procedure or a subsequent clinical procedure. The second fistula can be between the same two vascular locations as the first fistula, or one or both of the second fistula vascular locations can be different (e.g. a different vein and/or artery).

Figure 6:
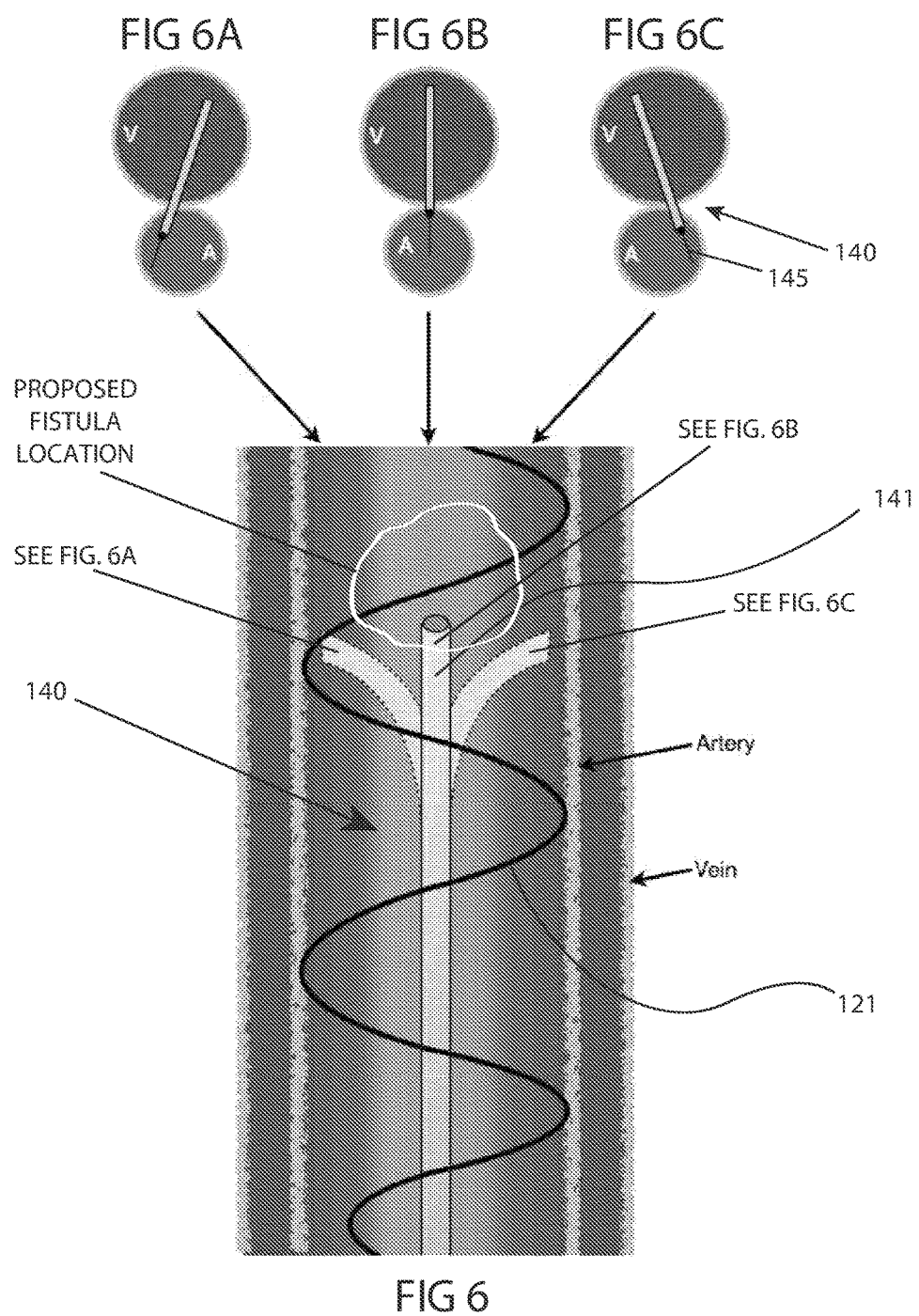
FIG. 6 is an angiographic view of a patient's vein and artery prior to advancement of a needle into the artery, consistent with the present inventive concepts.

Referring now to FIG. 6, an angiographic view of a patient's vein and artery prior to advancement of a needle into the artery is illustrated, such as may be performed in STEP 540 of the method of FIG. 5 described hereabove, consistent with the present inventive concepts. In the illustrated embodiment, a clinician has oriented an imaging device (e.g. a fluoroscope or other imaging device of FIG. 1), such that the segments of vein and artery at a proposed fistula location are overlapping (i.e. on top of each other in the image). The clinician has placed a target wire, such as target wire 120 of FIG. 1, into a patient's artery such that the helical portion 121 of wire is positioned at the proposed fistula location. Additionally, needle deployment device 140 has been advanced intraluminally through the vein as shown such that its distal end is proximal to the proposed fistula location. A next step comprises advancing needle 145 toward the helical portion 121 of wire 120 at the proposed fistula location.

Prior to insertion of needle 145 into the artery, a clinician can rotate needle deployment device 140 such that the direction of the needle deployment device 140 curvature is viewed (i.e. a non-linear, curved segment is visualized) on the imaging apparatus. Confirming the direction of curvature ensures that needle 145 is to be advanced in the desired direction, such as into the center of the artery. For example, if a clinician rotates needle deployment device 140 such that its tip is positioned as shown in FIG. 6A or 6C, a clinician will be aiming to an off-center location of the patient's artery. If a clinician rotates needle deployment device 140 such that its tip is positioned as shown if FIG. 6B, needle 145 will subsequently be advanced into the relative center of the patient's artery. The radius of curvature of a needle deployment device 140 can be reduced (e.g. by manual reshaping or by selected a different needle deployment device 140) if a clinician has difficulty in aiming needle 145 at the center of the artery prior to insertion. Conversely, the radius of curvature of needle deployment device 140 can be increased to create a more desirable needle 145 advancement trajectory.

Figure 7:
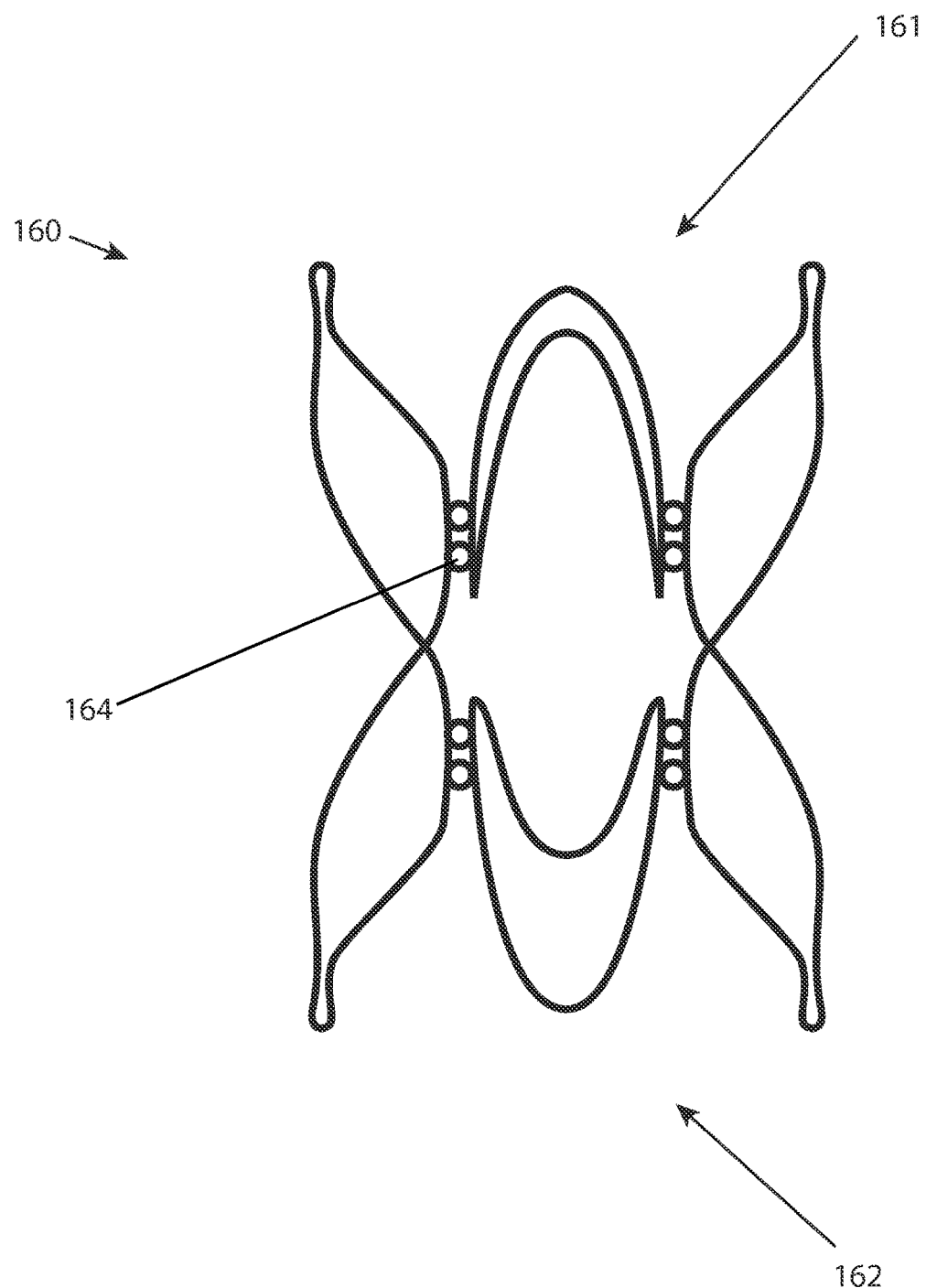
FIG. 7 is a perspective view of an anastomotic clip, consistent with the present inventive concepts.

Referring now to FIG. 7, a perspective view of an anastomotic clip is illustrated, consistent with the present inventive concepts. Clip 160 can comprise at least two distal arms 161 and at least two proximal arms 162. In the illustrated embodiment, clip 160 comprises four distal arms 161 and four proximal arms 162.

Clip 160 can be formed from a single tube of resilient material, such as nickel titanium alloy, spring steel, glass or carbon composites or polymers, or pseudoelastic (at body temperature) material such as nickel titanium alloy or comparable alloys and polymers, by laser cutting several closed-ended slots along the length of the tube (leaving the extreme distal and proximal edges of the tube intact) and cutting open-ended slots from the longitudinal center of the tube through the distal and proximal edges of the tube. The open-ended slots are cut between each pair of closed-end slots to form a number of loops joined at the center section by waist segments. Many other fabrication techniques can be utilized, for example, clip 160 can be made of several loops of wire welded together at the waist section.

After the tube is cut as described above, it is formed into its eventual resiliently expanded configuration. In this configuration, the loops turn radially outwardly from the center section, and evert toward the center plane of the center section, thus forming clinch members, i.e. distal arms 161 and proximal arms 162, in the form of arcuate, everted, petaloid frames at either end of the loop, extending from the generally tubular center section formed by waist segments. For clarity, the term everted is used here to mean that the arc over which the petaloid frame runs is such that the inside surface of clip 160 faces radially outwardly from the cylinder established by the tube.

Once clip 160 has resiliently expanded to the extent possible given its impingement upon the walls of the starting vessel and the target vessel, the center section can be further expanded by plastic deformation. This can be accomplished by inflating a balloon, not shown, within the center section and expanding the center section beyond its elastic or superelastic deformation range. By plastically deforming the center section of clip 160, the center section becomes more rigid and able to withstand the compressive force of the walls of the starting and target vessels.

As illustrated, the construction provides several pairs of longitudinally opposed (that is, they bend to come into close proximity to each other, and perhaps but not necessarily, touch) and aligned (they are disposed along the same longitudinal line) distal arms 161 and proximal arms 162. Overall, the petaloid frames of distal arms 161 form a "corolla," analogous to the corolla of a flower, flange or rivet clinch, which impinges on the starting vessel wall and prevents expulsion into the target vessel, and the petaloid frames of proximal arms 162 form a corolla, flange or rivet clinch (this clinch would be analogous to a rivet head, but it is formed like the clinch after insertion of the rivet), which impinges on the target vessel wall and prevents the expulsion of clip 160 into the target vessel. Also, the central section forms a short length of rigid tubing to keep the fistula open. The resilient apposition of the at least two distal arms 161 and at least two proximal arms 162 will securely hold clip 160 in place by resiliently clamping the walls of the starting vessel and the target vessel, even over a considerable range of wall thickness or "grip range."

The respective lengths of arms 161 and 162 can be variably sized to maximize or optimize the stability of clip 160 with respect to the vessels when deployed between adjacent vessels. Moreover, varying the lengths of the respective arms can further provide additional advantages. For instance, the arms which are shortened in length can facilitate the positioning and securement of clip 160 between the vessels by allowing for the relatively shorter member to swing into position within the vessel lumen during deployment, as described in further detail below. Additionally, a shorter member can provide for a minimized implant size when placed against the vessel interior wall for securement as well as a mitigating any physiologic reaction to the implant, e.g., a reduction in thrombosis, etc. Additionally, arms 161 and/or 162 which are lengthened relative to other arms can provide for increased clip stability by increasing the amount of force applied against the tissue walls.

Moreover, arms having different lengths can additionally place the adjacent vessels in tension such that the vessel walls are drawn towards one another and arms 161 and/or 162 contact the vessel luminal walls to stabilize not only clip 160 within the vessels but also the vessels with respect to one another. Additionally, having one or more arms, such as distal arms 161, sized to have a length shorter than its respective apposed clinch member can also facilitate the deployment and/or positioning of distal arms 161 within the vessel since the shorter length clinch members can more easily "swing" through an arc within the vessel lumen without contacting the interior walls. Arms with differing lengths can further be configured to align along different planes when deployed to facilitate vessel separation, if so desired.

Clip 160 can further comprise at least one marker, not shown, configured to rotationally position the clip at the fistula location. For example, a marker can be oriented toward the target vessel prior to deployment of clip 160. Alternatively or additionally, a marker can be oriented based upon a patient image, e.g. a real-time fluoroscopy image. In yet another embodiment, clip 160 can comprise at least one marker configured to longitudinally position the clip at the fistula location. A marker can indicate the distal and/or proximal end of clip 160.

Clip 160 can further comprise holes 164 configured to engage a clip delivery catheter projection such as to allow the shaft of the clip deployment catheter, not shown, to be retracted while clip 160 remains positioned in the distal portion of the shaft. In one embodiment, holes 164 are constructed and arranged about the clip asymmetrically such that clip 160 can be attached in the proper orientation.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. A method of treating a patient comprising:
   selecting a patient having a cardiac valve requiring treatment; and
   creating a flow pathway between a first vascular location in an artery selected from the group consisting of an aorta, an axillary artery, a brachial artery, an ulnar artery, a radial artery, a profundal artery, a femoral artery, an iliac artery, a popliteal artery, and a carotid artery and a second vascular location in a vein selected from the group consisting of an inferior vena cava, a saphenous vein, a femoral vein, an iliac vein, a popliteal vein, a brachial vein, a basilica vein, a cephalic vein, a medial forearm vein, a medial cubital vein, an axillary vein, and a jugular vein;
   wherein the method is constructed and arranged to treat a cardiac structure comprising a cardiac valve and to reduce a patient parameter selected from a group consisting of peripheral vascular resistance, left ventricular pre-load, left ventricular pressure, left atrial volume, left atrial stretching: and combinations thereof.

2. The method of claim 1, wherein the method treats regurgitation of a cardiac valve selected from the group consisting of: mitral valve; aortic valve;
   and combinations thereof.

3. The method of claim 1, wherein the method treats a patient cardiac valve condition selected from the group consisting of: valve regurgitation; valve insufficiency; chronic high left heart pressures; and combinations thereof.

4. The method of claim 1, wherein the flow pathway comprises an anatomical location relatively proximate to a kidney of the patient.

5. The method of claim 1, wherein the flow pathway comprises an anatomical location positioned at a location that comprises an infrarenal anatomical location.

6. The method of claim 5, wherein the first vascular location comprises an artery.

7. The method of claim 1, wherein the flow pathway comprises an anatomical location positioned at a location that comprises a supra-renal anatomical location.

8. The method of claim 7, wherein the first vascular location comprises an artery.

9. The method of claim 1, wherein the first vascular location comprises a chamber of the heart.

10. The method of claim 9, wherein the first vascular location comprises the left atrium and the second vascular location comprises the right atrium.

11. The method of claim 9, wherein the first vascular location comprises the left ventricle and the second vascular location comprises the coronary sinus.

12. The method of claim 1, wherein further comprising performing a valvuloplasty procedure on the cardiac valve.

13. The method of claim 1, further comprising dilating the flow pathway.

14. The method of claim 13, wherein the dilation is performed by inflating a balloon in the flow pathway.

15. The method of claim 13, wherein the dilation is performed at a diameter between 3 mm and 5 mm.

16. The method of claim 15, wherein the dilation is performed at a diameter of approximately 4 mm.

17. A method of treating a patient comprising:
    selecting a patient having a cardiac valve requiring treatment; and creating a flow pathway between a first vascular location in an artery selected from the group consisting of an aorta, an axillary artery, a brachial artery, an ulnar artery, a radial artery, a profundal artery, a femoral artery, an iliac artery, a popliteal artery; and a carotid artery and a second vascular location in a vein selected from the group consisting of an inferior vena cava, a saphenous vein, a femoral vein, an iliac vein, a popliteal vein; a brachial vein, a basilica vein, a cephalic vein, a medial forearm vein, a medial cubital vein, an axillary vein, and a jugular vein; and performing a valvuloplasty procedure on the cardiac valve.

* * * * *